US010905756B2

(12) United States Patent
Eichmeyer et al.

(10) Patent No.: US 10,905,756 B2
(45) Date of Patent: *Feb. 2, 2021

(54) BIVALENT SWINE INFLUENZA VIRUS VACCINE

(71) Applicant: Boehringer Ingelheim Vetmedica GmbH, Ingelheim am Rhein (DE)

(72) Inventors: Marc Allan Eichmeyer, Bondurant, IA (US); Wesley Scott Johnson, Ames, IA (US); Eric Martin Vaughn, Ames, IA (US); Michelle L. Walz, Ankeny, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/015,512

(22) Filed: Jun. 22, 2018

(65) Prior Publication Data

US 2018/0289795 A1 Oct. 11, 2018

Related U.S. Application Data

(63) Continuation of application No. 15/050,640, filed on Feb. 23, 2016, now Pat. No. 10,029,005.

(60) Provisional application No. 62/121,181, filed on Feb. 26, 2015.

(51) Int. Cl.
| | | |
|---|---|---|
| *A61K 39/145* | (2006.01) | |
| *A61K 39/00* | (2006.01) | |
| *A61K 39/12* | (2006.01) | |
| *C12N 7/00* | (2006.01) | |
| *C07K 14/005* | (2006.01) | |

(52) U.S. Cl.
CPC .......... *A61K 39/145* (2013.01); *A61K 39/12* (2013.01); *C07K 14/005* (2013.01); *C12N 7/00* (2013.01); *A61K 2039/525* (2013.01); *A61K 2039/5254* (2013.01); *A61K 2039/54* (2013.01); *A61K 2039/543* (2013.01); *A61K 2039/55* (2013.01); *A61K 2039/552* (2013.01); *A61K 2039/70* (2013.01); *C12N 2760/16034* (2013.01); *C12N 2760/16121* (2013.01); *C12N 2760/16134* (2013.01)

(58) Field of Classification Search
CPC .......... C12N 2760/16134; C12N 7/00; A61K 39/12; A61K 39/145; C07K 14/005
See application file for complete search history.

(56) References Cited

U.S. PATENT DOCUMENTS

| | | | | |
|---|---|---|---|---|
| 8,124,101 B2* | 2/2012 | Palese | ................. | A61K 39/145 424/206.1 |
| 2013/0115235 A1* | 5/2013 | Jin | ........................... | C12N 7/00 424/186.1 |

FOREIGN PATENT DOCUMENTS

| | | |
|---|---|---|
| CN | 102166352 A | 8/2011 |
| CN | 103468647 A | 12/2013 |

OTHER PUBLICATIONS

Vincent et al., "Live attenuated influenza vaccine provides superior protection from heterologous infection in pigs with maternal antibodies without inducing vaccine associated enhanced respiratory disease." Journal of virology (2012): JVI-01439.
Pyo et al., "Protective efficacy of intranasally administered bivalent live influenza vaccine and immunological mechanisms underlying the protection." Vaccine 32, No. 30 (2014): 3835-3842.
Masic et al., "Elastase-dependent live attenuated swine influenza A viruses are immunogenic and confer protection against swine influenza A virus infection in pigs." Journal of virology 83, No. 19 (2009): 10198-10210.
Masic et al., "Immunogenicity and protective efficacy of an elastase-dependent live attenuated swine influenza virus vaccine administered intranasally in pigs." Vaccine 28, No. 43 (2010): 7098-7108.

* cited by examiner

*Primary Examiner* — Barry A Chestnut
(74) *Attorney, Agent, or Firm* — Suzanne Shope; John Ezcurra

(57) ABSTRACT

The present invention relates to an immunogenic composition comprising: a) a modified live H3 virus of swine influenza, and b) a modified live H1 virus of swine influenza. Furthermore, the present invention relates to methods for immunizing a subject comprising administering to such subject the immunogenic composition of the present invention. Moreover, the present invention relates to methods of treating or preventing clinical signs caused by swine influenza virus in a subject of need, the method comprising administering to the subject a therapeutically effective amount of an immunogenic composition according to the present invention.

26 Claims, No Drawings
Specification includes a Sequence Listing.

BIVALENT SWINE INFLUENZA VIRUS VACCINE

CROSS-REFERENCE TO RELATED APPLICATIONS

This application is a continuation of U.S. patent application Ser. No. 15/050,640, filed Feb. 23, 2016, now U.S. Pat. No. 10,029,005, which claims the benefit of U.S. Patent Application No. 62/121,181, filed Feb. 26, 2015, the entire contents of which are hereby incorporated by reference herein.

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Influenza infection in pigs was first reported in 1918 and the first swine influenza viruses were isolated from pigs in 1930 (Shope, R. E., 1931, J. Exp. Med. 54:373-385). Swine influenza (SI) is an acute respiratory disease of swine caused by type A and C influenza viruses. Its severity depends on many factors, including host age, virus strain, and secondary infections (Easterday, 1980, Philos Trans R Soc LondB Biol Sci 288:433-7). Before 1998, mainly "classical" H1N1 SI viruses (SIV) were isolated from swine in the United States (Kida et al, 1994, J Gen Virol 75:2183-8; Scholtissek, 1994, Eur J Epidemiol 10:455-8; Olsen et al, 2000, Arch Virol. 145:1399-419). In 1998, SIVs of the subtype H3N2 were isolated in multiple states in the United States.

SIV replication is limited to epithelial cells of the upper and lower respiratory tract of pigs, the nasal mucosa, ethmoid, tonsils, trachea, and lungs, and virus excretion and transmission occur exclusively via the respiratory route. Infectious virus can thus be isolated from the tissues mentioned, as well as from tonsils, bronchoalveolar lavage (BAL) fluid, and nasal, tonsillar, or oropharyngeal swabs (Kristien Van Reeth and Wenjun Ma, 2013, Current Topics in Microbiology and Immunology 370: 173-200).

The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules of linear, negative polarity, single-stranded RNAs which encode eleven polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1), nuclear export protein (NEP); and the proapoptotic factor PB1-F2.

The type A influenza viruses are divided into 17 H (hemagglutinin) and 10 N (Neuraminidase) subtypes which can give rise to many possible combinations (designated as H1N1, H1N2, H2N1, H2N2, H5N1, H5N2 and so on) (Tong et al., 2012, Proc. Natl. Acad. Sci. USA, 109: 4269-4274). The hemagglutinin (HA) plays role in attachment of the virus to the surface of infected cells while the neuraminidase (NA) plays role in release of the progeny viruses from the infected cells therefore NA plays role in spread of the virus (Wang et al., 2009, Biochem. Biophys. Res. Commun., 386: 432-436).

The pathogenicity of influenza viruses is modulated by multiple virus and host factors. Among the host factors that fight virus infections, the type I interferon (IFN[alpha]/[beta]) system represents a powerful antiviral innate defense mechanism which was established relatively early in the evolution of eukaryotic organisms (Garcia-Sastre, 2002, Microbes Infect 4:647-55). Influenza A viruses express a non-structural protein in infected cells, the NS1 protein which counteracts the cellular IFN[alpha]/[beta] response (Garcia-Sastre et al., 1998, Virology 252:324-30).

Modification of the NS1 can be utilized to produce live attenuated SIVs as described by Solórzano et al. 2005 (J Virol 79:7535-7543), Vincent et al 2012 (Journal of Virology 19: 10597 to 10605) and in WO 2006/083286 A2. Attenuated SIVs expressing NS1-truncated proteins of an H3N2 SIV (sw/Texas/4199-2/98, Tx/98) with 73, 99, or 126 amino acids (Tx/98 NS1D73, Tx/98 NS1D99, and Tx/98 NS1D126) have been generated using reverse genetics.

However, commercial vaccines currently available against swine influenza virus (SIV) are inactivated, adjuvanted, whole virus vaccines, based on H1N1 and/or H3N2 and/or H1N2 SIVs for intramuscular injection (Kristien Van Reeth and Wenjun Ma, 2013, Current Topics in Microbiology and Immunology 370: 173-200). In sow herds with high antibody levels to SIV from either vaccination and/or natural infection, vaccination of piglets should be delayed until the age of 12-16 weeks to avoid interference with maternally derived antibodies (MDA).

There are two major weaknesses of the immune response induced by killed virus vaccines. First, such vaccines induce only serum antibodies, no mucosal antibodies and, further, the vaccine induced serum HI antibody titers decline rapidly between 2 and 6 weeks after the booster vaccination. Second, inactivated vaccines in general do not enter the endogenous pathway of antigen presentation and are unable to activate virus-specific CD8+ T cells or a CTL response.

Further, when combining different antigens for generating a combination vaccine the efficacy of the single components may be affected by a phenomenon called interference.

A further problem arises as most SIV vaccines are used for sow vaccination resulting in long lasting maternal SIV antibodies in piglets (Markowska-Daniel et al., 2011, Veterinary Immunology and Immunopathology, 142: 81-86). Regarding this, vaccination of piglets may be difficult to combine with vaccination of sows because of prolonged maternal immunity.

Thus, there is a need for SIV vaccines being highly efficacious and administrable early in age.

DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

The present invention solves the problems inherent in the prior art and provides a distinct advance in the state of the art. Generally, the present invention provides an immunogenic composition comprising: a) a modified live H3 virus of swine influenza, and b) a modified live H1 virus of swine influenza.

Advantageously, the experimental data provided by the present invention disclose safety and efficacy and several advantageous effects of the immunogenic composition provided herein. In particular, the data provided herein show a lack of interference between the two modified live H3 and H1 viruses of swine influenza components. Further, the experimental data provided herein clearly provide evidence that the two modified live H3 and H1 viruses of swine influenza components act synergistically together.

Further, a cross-protection effect has been observed for the bivalent vaccine of the present invention.

Additionally, the experimental data provided by the present invention disclose safety and efficacy of the immunogenic composition provided herein when administered to piglets early in age (piglets being a few days of age) and piglets having maternally derived antibodies. Thus, no interference of the immunogenic composition provided herein with maternally derived antibodies have been observed.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a SIV infection. The host is also described as "subject". Preferably, any of the hosts or subjects described or mentioned herein is an animal.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

The term "infection" or "infected" refer to the infection of a subject by SIV.

The term "swine influenza virus" is known by the person skilled in the art. The term swine influenza virus refers to a type A or type C influenza virus from the family orthomyxovirus that causes swine influenza. While orthomyxovirus has three groups: type A, type B and type C, only type A and type C influenza viruses infect pigs. Subtypes of swine influenza virus include H1N1, H1N2, H3N2, and H3N1. H9N2 and H5N1 can also be found in pigs. Preferably, a swine influenza virus is an influenza virus that has been isolated from swine. A swine influenza virus contains a swine NS1 gene. Representative swine NS1 genes can be found in public sequence databases such as Genbank and include, but are not limited to, Genbank Accession No. AJ293939 (A/swine/Italy/13962/95(H3N2)) and Genbank Accession No. AJ344041 (A/swine/Cotes d'Armor/1121/00 (H1N1)). Examples of swine influenza virus variants include, but are not limited to, A/Swine/Colorado/1/77, A/Swine/Colorado/23619/99, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/985 A/Swine/Wisconsin/458/98, A/Swine/Wisconsin/464/98 and A/Swine/Wisconsin/14094/99.

The term "H1N1" and "H3N2" is known by the person skilled in the art. However, in general, type A influenza viruses are divided into 17 H (hemagglutinin) and 10 N (Neuraminidase) subtypes which can give rise to many possible combinations (designated as H1N1, H1N2 . . . H2N1, H2N2 . . . H5N1, H5N2 . . . and so on). Thus, the terms "H1N1" and "H3N2" refer to a specific combination of hemagglutinin (HA) and neuraminidase (NA) subtypes of the SIV.

The term "NS1" is known by the person skilled in the art. In particular, "NS1" refers to the gene which encodes the nonstructural protein (NS1) in influenza. NS1 is one of the eight molecules encoded by the segmented genome of influenza A and other viruses. Representative swine NS1 genes can be found in public sequence databases such as Genbank and include, but are not limited to, Genbank Accession No. AJ293939 (A/swine/Italy/13962/95(H3N2)) and Genbank Accession No. AJ344041 (A/swine/Cotes d'Armor/1121/00(H1N1)). However, the term NS1 does not refer to the NS1 gene only, but also refers to NS1 gene products (such as RNA or protein) encoded by the NS1 gene. In the case of a protein, the NS1 gene product is full-length and has wild-type NS1 activity, (e.g., from Influenza A/swine/Texas/4199-2/98). The full length wildtype swine NS1 proteins vary between 217 to 237 amino acids. However, in most cases the full length wildtype swine NS1 protein is 219 amino acids. Further, the term "NS1 deletion" means that one or more amino acid are deleted within the NS1 protein and one or more nucleic acids are deleted within the NS1 gene or nucleotide sequence, respectively.

In one aspect of the present invention the modified live H3 and H1 viruses of swine influenza have a N (neuraminidase) subtype selected from the group consisting of N1, N2, N3, N4, N5, N6, N7, N8, N9 and N10.

In one aspect of the present invention the modified live H3 virus of swine influenza is H3N2 of swine influenza.

In one aspect of the present invention the modified live H1 virus of swine influenza is H1N1 of swine influenza virus.

In one aspect of the present invention the modified live H3 and H1 viruses of swine influenza have one or more mutations in the NS1 gene.

In one aspect of the present invention the modified live H3 and H1 viruses of swine influenza have a deletion within the NS1 gene.

In one aspect of the present invention the modified live H3 and H1 viruses of swine influenza are attenuated swine influenza viruses.

The term "attenuated" refers to a pathogen having a reduced virulence. In the present invention "attenuation" is synonymous with "avirulent". In the present invention, an attenuated SIV is one in which the virulence has been reduced so that it does not cause clinical signs of a swine influenza infection but is capable of inducing an immune response in the target mammal, but may also mean that the clinical signs are reduced in incidence or severity in animals infected with the attenuated SIV in comparison with a "control group" of animals infected with non-attenuated SIV and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group as defined above. Thus, an attenuated, avirulent SIV strain is one that suitable for incorporation into an immunogenic composition comprising a modified live SIV.

Thus, the present invention provides an immunogenic composition comprising a) an attenuated modified live H3 virus of swine influenza, and b) an attenuated modified live H1 virus of swine influenza.

Preferably, the term "attenuated", as mentioned herein, is particularly directed to a genetically engineered change in a genomic sequence, such as by truncation of the NS1 gene or protein, which in particular results in a virus growing to titers significantly lower than wild type swine influenza virus in the infected host, when propagated under the same conditions and/or having defective IFN antagonist activity.

In another aspect of the present invention the H3 and H1 viruses of swine influenza of the present invention have been inactivated resulting in whole inactivated viruses. Thus, the present invention also refers to an immunogenic composition comprising: a) an inactivated H3 virus of swine influenza, and b) an inactivated H1 virus of swine influenza. Preferably, the modified live H3 virus of swine influenza is a H3N2 of swine influenza and the modified live H1 virus of swine influenza is a H1N1 of swine influenza virus.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the H3N2 and H1N1 NS1 deletion mutants. In general, the inaction process is performed until no growth of the H3N2 and H1N1 NS1 deletion mutants can be detected in a suitable cultivation system.

Preferably, the inactivated H3 and H1 viruses of swine influenza are formalin inactivated, preferably using the concentrations as described hereinabove.

The inactivated H3 and H1 viruses of swine influenza of the invention may be incorporated into liposomes using known technology such as that described in Nature, 1974, 252, 252-254 or Journal of Immunology, 1978, 120, 1109-13. In another embodiment of the invention, the inactivated H3 and H1 viruses of swine influenza of the invention may be conjugated to suitable biological compounds such as polysaccharides, peptides, proteins, or the like, or a combination thereof.

In one aspect of the present invention the modified live H3 and H1 viruses of swine influenza are mutagenized viruses or reassortants.

The term "mutagenized virus" refers to a virus having mutation(s). The term "mutation" in the context of the invention is understood as a change in a genomic sequence, in particular in the RNA sequence of a swine influenza virus. For example, the mutant viruses can be generated by natural variation, exposure to UV irradiation, exposure to chemical mutagens, by passaging in non-permissive hosts, by reassortment (i.e., by coinfection of an attenuated segmented virus with another strain having the desired antigens), and/or by genetic engineering (e.g., using "reverse genetics").

Preferably, the mutation is a deletion of the NS1 gene or protein of the SIV.

The term "reassortant" refers to a swine influenza virus in which genome segments have been exchanged with another strain or subtype of a swine influenza virus. The swine influenza virus A has a segmented genome, therefore, the attenuated phenotype can be transferred to another strain by reassortment, (i.e., by coinfection of the attenuated virus and the desired strain, and selection for reassortants displaying both phenotypes). Thus, reassortment techniques can be used to transfer the attenuated phenotype from a parental swine influenza virus strain (a natural mutant, a mutagenized virus, or a genetically engineered virus) to a different virus strain (a wild-type virus, a natural mutant, a mutagenized virus, or a genetically engineered virus).

In one aspect of the present invention the modified live H3 and H1 viruses of swine influenza are genetically engineered.

The term "genetically engineered" refers to swine influenza viruses which have been mutated by using "reverse genetics" approaches. Preferably, the NS1 deletion mutant according to the present invention has been genetically engineered. The reverse genetics technique involves the preparation of synthetic recombinant viral RNAs that contain the non-coding regions of the swine influenza virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are well known to the person skilled in the art.

In one aspect of the present invention the modified live H3 and H1 viruses of swine influenza have an impaired interferon antagonist phenotype.

The term "impaired interferon antagonist phenotype" refers to a swine influenza virus having a reduced or inhibited cellular interferon immune response. Preferably, the swine influenza virus has a reduced or inhibited interferon expression and/or activity. Preferably, the expression and/or activity of one or two types of interferon (IFN) is reduced or inhibited. In one aspect of the present invention, the expression and/or activity of IFN-[alpha] is affected. In another aspect, the expression and/or activity of IFN-[beta] is affected. In another aspect, the expression and/or activity of IFN-[gamma] is affected. Preferably, the expression and/or activity of IFN-[beta] and/or IFN-[gamma] is reduced 5-10%, 10-20%, 20-30%, 30-40%, 40-50%, 50-60%, 60-70%, 70-80%, 80-90% or more by protein, polypeptide, etc. with an interferon antagonist activity when compared to a control (e.g., PBS or a protein without interferon antagonist activity) in IFN-competent systems, e.g., a wild-type cell or animal under the same conditions. More preferably, the expression and/or activity of IFN-[beta] and/or IFN-[gamma] is reduced approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by protein, polypeptide, etc. with an interferon antagonist activity when compared to a control (e.g., PBS or a protein without interferon antagonist activity) in IFN-competent systems under the same conditions.

Thus, in another aspect of the present invention the immunogenic composition comprises a) an attenuated modified live H3 virus of swine influenza, and b) an attenuated modified live H1 virus of swine influenza, whereby both components have a diminished ability of the NS1 gene products to antagonize the cellular interferon response.

In one aspect of the present invention the modified live H3 and H1 viruses of swine influenza have one or more mutations at the carboxy terminus of the NS1 protein.

The term "carboxy terminus" is well known to the person skilled in the art. The carboxy terminus is also termed carboxyl-terminus, C-terminus, C-terminal tail, C-terminal end, or COOH-terminus. When the protein is translated from messenger RNA, it is created from N-terminus to C-terminus. Thus, the carboxy terminus is the end of an amino acid chain (protein or polypeptide), terminated by a free carboxyl group (—COOH).

The term "mutation" already has been described above.

In one aspect of the present invention the modified live H3 and H1 viruses of swine influenza have a carboxy-terminal truncated NS1 protein.

The term "carboxy-terminal truncated" refers to the truncation of the NS1 protein of the carboxy terminus. The term "carboxy terminus" already has been described above. The term "truncated or truncation" refers to the deletion of one or more amino acid within the NS1 protein or the deletion of one or more nucleic acids within the NS1 gene or nucleotide sequence. Thus, portions of the amino terminal region of the NS1 gene product are retained whereas portions of the carboxy terminus region of the NS1 gene product are deleted.

Preferably, the attenuated swine influenza virus of the invention comprises a genome comprising a mutation in the NS1 gene resulting in a deletion consisting of 5, preferably 10, 15, 20, 25, 30, 35, 40, 45, 50, 55, 60, 65, 70, 75, 80, 85, 90, 91, 92, 93, 94, 95, 100, 105, 110, 115, 119, 120, 121, 125, 130, 135, 140, 145, 146, 147, 148, 150, 155, 160, 165, 170 or 175 amino acid residues from the carboxy terminus of NS1 or a deletion of between 5-170, 25-170, 50-170, 100-170, 90-160, 100-160 or 105-160, 90-150, 5-75, 5-50 or 5-25 amino acid residues from the carboxy terminus.

More preferably, the attenuated swine influenza virus of the invention comprises a genome comprising a mutation in the NS1 gene resulting in a deletion of all amino acid residues of the NS1 gene product except amino acid residues 1-130, amino acid residues 1-129, amino acid residues 1-128, amino acid residues 1-127, amino acid residues 1-126, amino acid residues 1-125, amino acid residues 1-124, amino acid residues 1-123, amino acid residues 1-122, amino acid residues 1-121, amino acid residues 1-120, amino acid residues 1-115, amino acid residues 1-110, amino acid residues 1-100, amino acid residues 1-99, amino acid residues 1-95, amino acid residues 1-85, amino acid residues 1-80, amino acid residues 1-75, amino acid residues 1-73, amino acid residues 1-70, amino acid residues 1-65 or amino acid residues 1-60, wherein the amino terminal amino acid is number 1.

In one aspect of the present invention the modified live H3 and H1 viruses of swine influenza have a carboxy-terminal truncated NS1 protein comprising NS1 amino acids 1 through 124, 1 through 125, 1 through 126, 1 through 127 or 1 through 128, wherein the amino terminal amino acid is number 1.

Thus, in another aspect of the present invention the immunogenic composition comprises a) an attenuated modified live H3 virus of swine influenza, and b) an attenuated modified live H1 virus of swine influenza, whereby both viruses have a carboxy-terminal truncated NS1 protein comprising NS1 amino acids 1 through 124, 1 through 125, 1 through 126, 1 through 127 or 1 through 128, wherein the amino terminal amino acid is number 1.

In one aspect of the present invention the modified live H3 and H1 viruses of swine influenza have a carboxy-terminal truncated NS1 protein comprising NS1 amino acids 1 through 126.

In one aspect of the present invention the modified live H3 and H1 viruses of swine influenza have a carboxy-terminal truncated NS1 protein resulting in a deletion of 91, 92, 93 or 94 amino acid residues from the carboxy terminus of NS1.

Deletions from the carboxy terminus include deletions consisting of 85 to 100, more preferably 90 to 95 and even more preferably, 91 to 94 amino acid residues from the carboxy terminus of the NS1 protein. Most preferably, 91, 92, 93 or 94 amino acid residues from the carboxy terminus of the NS1 protein are deleted. More preferably 93 amino acid residues from the carboxy terminus of the NS1 protein are deleted.

In one aspect of the present invention the modified live H3 and H1 viruses of swine influenza have a NS1 gene or protein from A/Swine/Texas/4199-2/98.

In one aspect of the present invention the modified live H3 virus of swine influenza encodes a carboxy-terminal truncated NS1 protein comprising NS1 amino acids 1 through 124, 1 through 125, 1 through 126, 1 through 127 or 1 through 128, wherein the amino terminal amino acid is number 1.

In another aspect of the present invention the modified live H3 virus of swine influenza encodes a carboxy-terminal truncated NS1 protein comprising NS1 amino acids 1 through 126, wherein the amino terminal amino acid is number 1.

In one aspect of the present invention the modified live H3 virus of swine influenza encodes a carboxy-terminal truncated NS1 protein resulting in a deletion of 91, 92, 93 or 94 amino acid residues from the carboxy terminus of NS1.

In one aspect of the present invention the modified live H3 virus of swine influenza is A/Swine/Texas/4199-2/98.

In one aspect of the present the modified live H3 virus of swine influenza is TX/98/del 126.

The term "TX/98/del 126" refers to the A/Swine/Texas/4199-2/98 strain having a NS1 deletion mutant encoding for a carboxy-terminal truncated NS1 protein comprising NS1 amino acids 1 through 126, wherein the amino terminal amino acid is number 1.

In one aspect of the present invention the modified live H3 virus of swine influenza contains the HA, NA, PB2, PB1, PA, NP, and M from A/Swine/Texas/4199-2/98 and the NS1-126 gene is from A/Swine/Texas/4199-2/98.

The term "HA, NA, PB2, PB1, PA, NP, and M" refers to the gene segments or genes of the swine influenza virus. In general, influenza A genomes contain eight gene segments encoding 11 proteins. These proteins include the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1), nuclear export protein (NEP); and the proapoptotic factor PB1-F2.

In one aspect of the present invention the modified live H3 virus of swine influenza is the H3N2 NS1 deletion mutant of swine influenza virus described in WO 2006/083286 A2 designated as TX/98/del126.

In one aspect of the present invention the modified live H3 virus of swine influenza: a. comprises a nucleic acid sequence of gene segments having the NA and HA genes whose cDNA has at least 70% identity to the nucleic acid sequence as set forth in SEQ ID NO:1 or SEQ ID NO:2, or b. comprises a nucleic acid sequence of gene segments having the NA and HA genes encoding NA and HA proteins having an amino acid sequence with at least 70% identity to the amino acid sequence as set forth in SEQ ID NO:3 or SEQ ID NO:4, or c. comprises a NA and HA protein having an amino acid sequence with at least 70% identity to the amino acid sequence as set forth in SEQ ID NO:3 or SEQ ID NO:4.

Preferably, the modified live H3 virus of swine influenza is characterized by comprising a nucleic acid sequence of gene segments having the NA and HA genes as set forth in SEQ ID NO:1 or SEQ ID NO:2, or by comprising a nucleic sequence of gene segments having the NA and HA genes encoding NA and HA proteins having an amino acid sequence as set forth in SEQ ID NO:3 or SEQ ID NO:4, or by comprising a NA and HA protein having an amino acid sequence as set forth in SEQ ID NO:3 or SEQ ID NO:4.

However, the modified live H3 virus of swine influenza shall also encompass variants of the swine influenza virus. Such variants have essentially the same immunological properties as the specific modified live H3 virus of swine influenza as characterized above (characterized by the SEQ ID NO's 1 to 4). The HA and NA surface glycoproteins in influenza A viruses refer the vaccine induced immunity and possess the immunological properties, respectively. The term "having essentially the same immunological properties" encompass (but is not restricted to) that said variants are essentially effective in treating or preventing the clinical signs caused by swine influenza virus infection as described below or in improving the efficacy parameters as described below.

Moreover, it is to be understood that a variant as referred to in accordance with the present invention shall comprise modified live H3 virus of swine influenza: a. comprising nucleic acid sequences of gene segments having the NA and HA genes whose cDNA has at least 70%, at least 75%, at least 80%, at least 85%, at least 90%, at least 91%, at least 92%, at least 93%, at least 94%, at least 95%, at least 96%, at least 97%, at least 98% or at least 99% identity to the nucleic acid sequence as set forth in SEQ ID NO:1 or SEQ ID NO:2, or b. comprising nucleic acid sequences of gene segments having the NA and HA genes encoding NA and HA proteins having amino acid sequences with at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:3 or SEQ ID NO:4, or c. comprising a NA and HA protein having an amino acid sequence with at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:3 or SEQ ID NO:4.

The term "gene or gene segments" is well known to the person skilled in the art. However, as set forth above influenza A genomes such as the genome of the SIV contains eight gene segments encoding 11 proteins.

The terms "NA and HA" already have been defined above. HA (hemagglutinin) and NA (neuraminidase) are surface glycoproteins in influenza A viruses such as SIV. Further, NA is the major antigenic target of neutralizing antibodies.

The term "nucleic acid sequence" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificial modified one such as biotinylated polynucleotides. Further, it is to be understood that the NA and HA proteins as mentioned above may be encoded by a large number of polynucleotides due to the degenerated genetic code. Further, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

The term "cDNA" refers to a complementary DNA which is synthesized from a messenger RNA (mRNA) template in a reaction catalyzed by the enzyme reverse transcriptase. However, the term "cDNA" is well known by the person skilled in the art.

The term "amino acid sequence", "polypeptide" and "protein" are used interchangeable. The term "amino acid sequence" refers to a sequence of amino acids composed of the natural occurring amino acids as well as derivatives thereof. The naturally occurring amino acids are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus).

The term "identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, N.J. (1994); Sequence Analysis in Molecular Biology, von Heinge, G., Academic Press (1987); Sequence Analysis Primer, Gribskov, M. and Devereux, J., eds., M. Stockton Press, N.Y. (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al. Nucleic Acids Research, 12(1): 387 (1984)), BLASTP, BLASTN and FASTA (Altschul, S. F. et al. J. Molec. Biol., 215:403-410 (1990). The BLASTX program is publicly available from NCBI and other sources (BLAST Manual, Altschul, S. et al. NCVI NLM NIH Bethesda, Md. 20894, Altschul, S. F. et al. J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence homology.

It has to be understood that the sequence identity values recited above in percent (%) are to be determined, preferably, over the entire sequence. However, the sequence identity values recited above in percent (%) may be determined, over fragments comprising at least 20, at least 50, at least 100, at least 250 or at least 500 consecutive nucleotides of any one of the aforementioned nucleic acid sequences or over fragments comprising at least 20, at least 30, at least 50, at least 80, at least 100 or at least 150 consecutive amino acids of any one of the aforementioned amino acid sequences.

In one aspect of the present invention the modified live H1 virus of swine influenza is a chimeric virus.

The term "chimeric virus" refers to a virus comprising one or more nucleotide sequences or gene segments of a modified live H1 virus of swine influenza or a H1N1 swine influenza virus and one or more nucleotide sequences or gene segments that are not from a modified live H1 virus of swine influenza or a H1N1 swine influenza virus, but from another virus. Preferably, the modified live H1 virus of swine influenza or H1N1 NS1 deletion mutant swine influenza virus comprises the hemagglutinin and neuraminidase gene segments from a H1N1 subtype but all other gene segments from another swine influenza virus having a different (not H1N1) HA and NA subtype. More preferably, said other virus is a H3N2 swine influenza virus.

In particular, reassortment techniques can be used to transfer the attenuated phenotype from a parental swine influenza virus strain (such as the carboxy-terminal truncated NS1 of the above described H3N2 SIV strain) to a different virus strain (such as a H1N1 wild type virus). Thus, by said technique swine influenza virus genomes can be generated in which genome segments have been exchanged with another strain or subtype of a swine influenza virus.

In one aspect of the present invention the modified live H1 virus of swine influenza comprises a carboxy-terminal truncated NS1 of a H3 SIV strain, preferably a carboxy-terminal truncated NS1 of a H3N2 SIV strain.

In one aspect of the present invention the modified live H1 virus of swine influenza encodes a carboxy-terminal truncated NS1 protein comprising NS1 amino acids 1 through 124, 1 through 125, 1 through 126, 1 through 127 or 1 through 128, wherein the amino terminal amino acid is number 1.

In another aspect of the present invention the modified live H1 virus of swine influenza encodes a carboxy-terminal truncated NS1 protein comprising NS1 amino acids 1 through 126, wherein the amino terminal amino acid is number 1.

In one aspect of the present invention the modified live H1 virus of swine influenza encodes a carboxy-terminal truncated NS1 protein resulting in a deletion of 91, 92, 93 or 94 amino acid residues from the carboxy terminus of NS1.

In one aspect of the present invention the modified live H1 virus of swine influenza is A/Swine/Texas/4199-2/98.

In one aspect of the present invention the modified live H1 virus of swine influenza comprises the hemagglutinin and neuraminidase gene segments from a H1N1 subtype.

In one aspect of the present invention the modified live H1 virus of swine influenza comprises the hemagglutinin and neuraminidase gene segments from A/swine/Minnesota/37866/1999.

In one aspect of the present invention the modified live H1 virus of swine influenza contains HA and NA from A/swine/Minnesota/37866/1999 (H1N1) and PB2, PB1, PA, NP, M from A/Swine/Texas/4199-2/98 (H3N2) and the NS1-126 gene is from A/Swine/Texas/4199-2/98 (H3N2).

In one aspect of the present invention the modified live H1 virus of swine influenza is a chimeric of A/swine/Minnesota/37866/1999 and TX/98/del 126.

In one aspect of the present invention the modified live H1 virus of swine influenza a. comprises a nucleic acid sequence of gene segments having the NA and HA genes whose cDNA has greater than 70% identity to the nucleic acid sequence as set forth in SEQ ID NO:5 or SEQ ID NO:6, or b. comprises a nucleic sequence of gene segments having the NA and HA genes encoding NA and HA proteins having an amino acid sequence with greater than 70% identity to the amino acid sequence as set forth in SEQ ID NO:7 or SEQ ID NO:8, or c. comprises a NA and HA protein having an amino acid sequence with greater than 70% identity to the amino acid sequence as set forth in SEQ ID NO:7 or SEQ ID NO:8.

Preferably, the modified live H1 virus of swine influenza is characterized by comprising a nucleic acid sequence of gene segments having the NA and HA genes as set forth by SEQ ID NO:5 or SEQ ID NO:6, or by comprising a nucleic sequence of the NA and HA genes encoding NA and HA proteins having an amino acid sequence as set forth by SEQ ID NO:7 or SEQ ID NO:8, or by comprising a NA and HA protein having an amino acid sequence as set forth by SEQ ID NO:7 or SEQ ID NO:8.

However, the modified live H1 virus of swine influenza shall also encompass variants of the swine influenza virus. Such variants have essentially the same immunological properties as the specific modified live H1 virus of swine influenza as characterized above (characterized by the SEQ ID NO's 5 to 8). The HA and NA surface glycoproteins in influenza A viruses refer the vaccine induced immunity and possess the immunological properties, respectively. The term "having essentially the same immunological properties" encompass (but is not restricted to) that said variants are essentially effective in treating or preventing the clinical signs caused by swine influenza virus infection as described below or in improving the efficacy parameters as described below.

Moreover, it is to be understood that a variant as referred to in accordance with the present invention shall comprise modified live H1 virus of swine influenza a. comprising nucleic acid sequences of gene segments having the NA and HA genes whose cDNA has at least 70%, at least 75%, at least 80%, at least 85%, at least 90%, at least 91%, at least 92%, at least 93%, at least 94%, at least 95%, at least 96%, at least 97%, at least 98% or at least 99% identity to the nucleic acid sequence as set forth in SEQ ID NO:5 or SEQ ID NO:6, or b. comprising nucleic sequences of gene segments having the NA and HA genes encoding NA and HA proteins having amino acid sequences with at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:7 or SEQ ID NO:8, or c. comprising a NA and HA protein having an amino acid sequence with at least at least 70%, at least 75%, at least 80%, at least 85%, at least 90%, 91%, at least 92%, at least 93%, at least 94%, at least 95%, at least 96%, at least 97%, at least 98% or at least 99% identity the amino acid sequence as set forth in SEQ ID NO:7 or SEQ ID NO:8.

Thus, in another aspect of the present invention the immunogenic composition comprises a) an attenuated modified live H3N2 virus of swine influenza, and b) an attenuated modified live H1N1 virus of swine influenza, whereby both viruses have a carboxy-terminal truncated NS1 protein comprising NS1 amino acids 1 through 124, 1 through 125, 1 through 126, 1 through 127 or 1 through 128, wherein the amino terminal amino acid is number 1.

Further, in another aspect of the present invention the immunogenic composition comprises a) an attenuated modified live H3N2 virus of swine influenza, and b) an attenuated modified live H1N1 virus of swine influenza, whereby the modified live H3N2 virus of swine influenza contains the HA, NA, PB2, PB1, PA, NP, and M from A/Swine/Texas/4199-2/98 and the NS1-126 gene is from A/Swine/Texas/4199-2/98, and, whereby the modified live H1N1 virus of swine influenza contains HA and NA from A/swine/Minnesota/37866/1999 (H1N1) and PB2, PB1, PA, NP, M from A/Swine/Texas/4199-2/98 (H3N2) and the NS1-126 gene is from A/Swine/Texas/4199-2/98 (H3N2).

It has furthermore been shown that one dose of the immunogenic composition of the present invention is effective after the administration of such single dose of such immunogenic composition.

In one aspect of the present invention the immunogenic composition is formulated for a single-dose administration.

Preferably, the single-dose has a total volume between about 0.2 ml and 2.5 ml, more preferably between about 0.2 ml and 2.0 ml, even more preferably between about 0.2 ml and 1.75 ml, still more preferably between about 0.2 ml and 1.5 ml, even more preferably between about 0.4 ml and 1.25 ml, even more preferably between about 0.4 ml and 1.0 ml with a single 0.5 ml dose or 1.0 ml dose being the most preferred. Most preferred the single-dose has a total volume of 0.5 ml, 1 ml, 1.5 ml or 2 ml.

It has furthermore been shown that one dose of the immunogenic composition of the present invention is effective after the administration of such single dose of such immunogenic composition.

In one aspect of the present invention the immunogenic composition is administered intranasal.

In one aspect of the present invention the immunogenic composition is safe for sows during pregnancy and lactation.

In one aspect of the present invention the immunogenic composition is safe for pigs within the first two weeks of age.

In one aspect of the present invention the immunogenic composition is safe for pigs within the first week of age.

In one aspect of the present invention the immunogenic composition is safe for pigs within the first day of age.

In one aspect of the present invention the immunogenic composition is safe for pigs at day 0 of age.

In one aspect of the present invention the immunogenic composition further comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In one aspect of the present invention the pharmaceutically acceptable carrier is phosphate buffered saline.

Preferably, the immunogenic composition further comprises sucrose gelatin stabilizer.

In one aspect of the present invention the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In one aspect of the present invention the immunogenic composition comprises 2 to 8 $\log_{10}$ of the modified live H1 virus of swine influenza and/or 2 to 8 $\log_{10}$ of the modified live H3 virus of swine influenza.

In one aspect of the present invention the immunogenic composition comprises 2 to 6 $\log_{10}$ of the modified live H1 virus of swine influenza and/or 2 to 6 $\log_{10}$ of the modified live H3 virus of swine influenza.

In one aspect of the present invention the immunogenic composition comprises 2 to 4 $\log_{10}$ of the modified live H1 virus of swine influenza and/or 2 to 4 $\log_{10}$ of the modified live H3 virus of swine influenza.

In one aspect of the present invention the immunogenic composition is a vaccine.

In one aspect of the present invention the immunogenic composition is a bivalent vaccine.

In one aspect of the present invention the immunogenic composition is effective in the treatment and/or prophylaxis of clinical signs caused by SIV in a subject of need.

The term "treatment and/or prophylaxis" refers to the lessening of the incidence of the particular SIV infection in a herd or the reduction in the severity of clinical signs caused by or associated with the particular SIV infection. Thus, the term "treatment and/or prophylaxis" also refers to the reduction of the number of animals in a herd that become infected with the particular SIV (=lessening of the incidence of the particular SIV infection) or to the reduction of the severity of clinical signs normally associated with or caused by a SIV infection in a group of animals which animals have received an effective amount of the immunogenic composition as provided herein in comparison to a group of animals which animals have not received such immunogenic composition.

The "treatment and/or prophylaxis" generally involves the administration of an effective amount of the immunogenic composition of the present invention to a subject or herd of subjects in need of or that could benefit from such a treatment/prophylaxis. The term "treatment" refers to the administration of the effective amount of the immunogenic composition once the subject or at least some animals of the herd is/are already infected with such SIV and wherein such animals already show some clinical signs caused by or associated with such SIV infection. The term "prophylaxis" refers to the administration of a subject prior to any infection of such subject with SIV or at least where such animal or none of the animals in a group of animals do not show any clinical signs caused by or associated with the infection by such SIV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular SIV infection in a herd or to reduce the severity of clinical signs of the particular SIV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular SIV.

The term "clinical signs" as used herein refers to signs of infection of a subject from SIV. The clinical signs of infection depend on the pathogen selected. Examples for such clinical signs include but are not limited to respiratory distress, otitis, roughened hair coat, slight fever, depression, and reduced appetite. However, the clinical signs also include but are not limited to clinical signs that are directly observable from a live animal. Examples for clinical signs that are directly observable from a live animal include nasal and ocular discharge, lethargy, coughing, wheezing, thumping, elevated fever, weight loss, dehydration, lameness, wasting, paleness of the skin, unthriftiness and the like.

Preferably, the clinical signs lessened in incidence or severity in a treated subject compared to subjects that are either not treated or treated with an immunogenic composition that was available prior to the present invention but subsequently infected by the particular SIV refer to less weight loss, a lower virus load, a reduction in lung lesions, a reduced shedding, a reduced rectal temperature, or combinations thereof.

The term "subject" refers to animals, preferably to mammals such as mice, rats, guinea pigs, rabbits, hamsters, swine, sheep, dogs, cats, horses, monkeys, or cattle and, also preferably, to humans. More preferably, the subject is a swine.

The term "in need" or "of need", as used herein means that the administration/treatment is associated with the boosting or improvement in health or clinical signs or any other positive medicinal effect on health of the animals which receive the immunogenic composition in accordance with the present invention.

In one aspect of the present invention the modified live H3 and H1 viruses of swine influenza act synergistically together.

In one aspect of the present invention the concentrations of the modified live H3 and H1 viruses of swine influenza are reduced compared to the concentration of the H3 virus of swine influenza in a monovalent immunogenic composition and the concentration of the H1 virus of swine influenza in a monovalent immunogenic composition.

In one aspect of the present invention the modified live H3 virus of swine influenza increases the protection against a heterologous challenge, provides a cross-protection effect.

In one aspect of the present invention the modified live H3 virus of swine influenza increases the protection against a H1 challenge.

In one aspect of the present invention the modified live H3 virus of swine influenza increases the protection against a H1N1 challenge.

In one aspect of the present invention the modified live H3 virus is a H3N2 virus, preferably a H3N2 NS1 deletion mutant of swine influenza virus as described herein.

The present invention also relates to a method of immunizing a subject, comprising administering to a subject any of the immunogenic compositions as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular SIV infection in a herd or in the reduction in the severity of clinical signs caused by or associated with the particular SIV infection.

Further, the immunization of a subject in need with the immunogenic compositions as provided herewith, results in preventing infection of a subject by SIV infection. Even more preferably, immunization results in an effective, long-lasting, immunological-response against SIV infection. It will be understood that the said period of time will last more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a herd are effectively immunized.

Preferably, a herd of subjects is envisaged in this context which normally, i.e. without immunization, would develop clinical signs normally caused by or associated with a SIV infection. Whether the subjects of a herd are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular SIV.

The present invention also relates to a method of treating or preventing clinical signs caused by swine influenza virus in a subject of need, the method comprising administering to the subject a therapeutically effective amount of an immunogenic composition as described herein.

The terms "treating or preventing", "clinical signs", "subject" "of need" and "effective amount" have been defined elsewhere.

The present invention also relates to a method of reducing the viral shedding in a subject of need, in comparison to a subject of a non-immunized control group of the same species, the method comprising administering to the subject a therapeutically effective amount of an immunogenic composition as described herein.

The term "reducing" means, that the shedding is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular SIV. It is in the general knowledge of a person skilled in the art how to measure the viral shedding.

The present invention also relates to a method of reducing the viral shedding in a subject of need, in comparison to a subject of an immunized control group of the same species immunized with an immunogenic composition comprising a monovalent modified live H3 or H1 virus of swine influenza, the method comprising administering to the subject a therapeutically effective amount of an immunogenic composition as described herein.

The term "reducing" means, that the shedding is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% and most preferably by 100% in comparison to subjects immunized with an immunogenic composition comprising a monovalent NS1 deletion mutant of Swine Influenza virus but subsequently infected by the particular SIV. It is in the general knowledge of a person skilled in the art how to measure the viral shedding.

The term "shedding" refers to secretions such as nasal discharges and, further, to aerosols created by coughing or sneezing. Thus, shedding may be determined by examining the virus titer in nasal swabs or by the virus titer in the lungs. The term "shedding" further encompasses the transfer of virus to susceptible animals (i.e. sentinels). It is in the general knowledge of a person skilled in the art how to measure the viral shedding.

The term "a monovalent modified live H3 or H1 virus of swine influenza" refers to any SIV virus having H3 and H1 and being a modified live virus. Preferably, the term "a monovalent modified live H3 or H1 virus of swine influenza" refers to any SIV virus having a deletion in the NS1 protein. Further, the term monovalent is equivalent to univalent and refers to only a single SIV NS1 deletion mutant in comparison to multivalent vaccines such as bivalent or trivalent vaccines. Preferably, the monovalent modified live H3 or H1 virus of swine influenza is the H1N1 or H3N2 deletion mutant of Swine Influenza virus described herein. Most preferably, the monovalent NS1 deletion mutant of Swine Influenza virus is the H1N1 deletion mutant of Swine Influenza virus described herein.

In one aspect of the present invention the monovalent modified live H3 or H1 virus of swine influenza is a H1N1 NS1 deletion mutant of swine influenza virus.

In one aspect of the present invention the monovalent modified live H3 or H1 virus of swine influenza is the H1N1 NS1 deletion mutant of swine influenza virus as described herein.

In one aspect of the present invention the monovalent modified live H3 or H1 virus of swine influenza is a H3N2 NS1 deletion mutant of swine influenza virus.

In one aspect of the present invention the monovalent modified live H3 or H1 virus of swine influenza is the H3N2 NS1 deletion mutant of swine influenza virus as described herein.

The present invention overcomes deficiencies of the prior art and provides novel methods for providing increased swine protection against SIV. In particular, the present invention provides a method of administering an immunologically effective amount of vaccine to sows, and/or young piglets within days after birth, in order to immunize them against SIV.

The present invention also relates to a method of vaccinating a subject having anti-SIV antibodies comprising the step of administering to said animal a single effective dose of an immunogenic composition as described herein.

The term "anti-SIV antibodies" refers to antibodies that are specific towards SIV. Examples of such anti SIV antibodies comprise, but are not limited to maternally derived antibodies by vaccination of sows with a SIV vaccine or to maternally derived antibodies by SIV infection of sows. Further, the anti-SIV antibodies in the piglet may have been developed in response to a SIV infection of the piglet. The term "anti-SIV antibodies" shall further mean, but is not limited to, a piglet that has or is exposed to (passive transfer of maternally antibodies) a detectable anti-SIV antibody titer, preferably of at least 1:10, more preferably of more than 1:20, even more preferably of more than 1:40, even more preferably of more than 1:80, even more preferably of 1:160, even more preferably of more than 1:320, and most preferably of more than 1:640. Preferably, that anti-SIV antibody titer is detectable and quantifiable in a specific anti-SIV immune assay.

Preferably, the anti-SIV antibodies in the piglet have been developed in response to a SIV infection by the piglet. However, more preferably, those anti-SIV antibodies are maternally derived antibodies developed in response to vaccination of sows with a SIV vaccine or in response to a SIV infection of sows. The maternally derived antibodies are passively transferred to piglets via colostrum and milk.

Interference of maternally derived antibodies with vaccine antigen may reduce or even eliminate the immune response against live, as well as inactivated vaccines. Various degrees of interference of vaccine-induced immune responses by maternally derived antibodies have been reported for live vaccines, as well as for nonreplicating ones (i.e. inactivated or subunit vaccines) (Markowska-Daniel et al., 2011, Veterinary Immunology and Immunopathology, 142: 81-86). Optimally, vaccination of animals should begin just at the time of disappearance of maternal antibodies, but this approach may be impracticable due to a high degree of variability between individuals (Monteil et al., 1997).

Therefore, current vaccination strategies for immunization against SIV involve administration of the vaccine to pigs from only two to three weeks of age and older, because piglets below this age group could have maternal antibodies positive for SIV due to previous sow exposure or vaccination. Prior to the method of the present invention it was believed that the presence of maternal antibodies or other lactogenic factors could potentially interfere with the efficacy of vaccinations in such piglets, because the maternal antibodies have the ability to neutralize the vaccine before the piglet's immune system can recognize it and begin secreting its own antibodies. Therefore, vaccination of young piglets has been avoided in the face of maternal immunity.

To face this problem several vaccination strategies foresee a two shot vaccination regime for young animals: The first vaccination is given early in age in order to protect those animals with low maternally derived antibodies. It is accepted that this first vaccination may not be effective in animals with high maternally derived antibody titers due to an interference with the vaccine antigen. In order to also protect these animals, a second vaccination is required, when high maternally derived antibody levels are expected to have declined.

Advantageously, the experimental data provided by the present invention disclose safety and efficacy of the immunogenic composition provided herein when administered to piglets having maternally derived antibodies being a few days of age. In fact, piglets vaccinated within days after birth, as described herein, have reduced clinical signs associated with the disease compared to non-vaccinated piglets.

The present invention also relates to a method for preventing or reducing early SIV infections in a subject, the method comprising administering to the subject a therapeutically effective amount of an immunogenic composition as described herein.

Advantageously, the experimental data provided by the present invention disclose safety and efficacy of the immunogenic composition provided herein when administered to piglets being a few days of age and piglets having maternally derived antibodies. However, current vaccination strategies for immunization against SIV involve administration of the vaccine to pigs from only two to three weeks of age and older, because piglets below this age group could have maternal antibodies positive for SIV due to previous sow exposure or vaccination. Thus, the present invention further refers to a method for preventing or reducing early SIV infections in a subject.

Preferably, the pig to be immunized is 1, 2, 3, 4, 5, 6, 7, 8, 9, 10, 11, 12, 13, 14, 15, 16, 17, 18, 19, 20 or 21 days of age. More preferably, said pig to be immunized is 1, 2, 3, 4, 5, 6, 7, 8, 9, 10, 11, 12, 13, 14, 15, 16, 17, 18, 19, 20 or 21 days of age. Most preferably, said pig to be immunized is 1, 2, 3, 4, 5, 6 or 7 days of age.

However, it has to be understood that after vaccination of piglets being a few days of age, it does need several days for the immune system of the piglet to build up immunity against an SIV infection. Therefore, preferably, the piglets are immunized within the first 24 h of age.

However, more preferably, the pregnant sow is at least vaccinated one time before farrowing with the immunogenic composition described herein, and further, the born piglet is vaccinated within days (preferably within the first week of age or within the first 24 h of age) with the immunogenic composition described herein. Thus, the piglet is already protected by maternal derived immunity and, further, will be protected by vaccine induced immunity.

The term "early SIV infection" refers to a SIV infection early in age of a pig. A SIV infection early in age refers to an animal having a SIV infection within the first four weeks of age, more preferably within the first three weeks of age, most preferably between the first two weeks of age.

The term "reducing" means, that the early SIV infection is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% and most preferably by 100% in comparison to a subject of a non-immunized control group of the same species.

In another aspect of the present invention said subject is selected from the list consisting of swine, cattle, cat and dog.

In one aspect of the present invention the immunogenic composition is administered once.

It is understood, that a single-dose is administered only once. As shown in the Examples the immunogenic composition as provided herein has been proven to be efficacious after the administration of a single dose to a subject of need.

Preferably, the single-dose has a total volume between about 0.2 ml and 2.5 ml, more preferably between about 0.2 ml and 2.0 ml, even more preferably between about 0.2 ml and 1.75 ml, still more preferably between about 0.2 ml and 1.5 ml, even more preferably between about 0.4 ml and 1.25 ml, even more preferably between about 0.4 ml and 1.0 ml with a single 0.5 ml dose or 1.0 ml dose being the most preferred. Most preferred the single-dose has a total volume of 0.5 ml, 1 ml, 1.5 ml or 2 ml.

In one aspect of the present invention the immunogenic composition is administered at two or more doses.

However, the immunogenic composition can be administered at two or more doses, with a first dose being administered prior to the administration of a second (booster) dose. Preferably, the second dose is administered at least 15 days after the first dose. More preferably, the second dose is administered between 15 and 40 days after the first dose. Even more preferably, the second dose is administered at least 17 days after the first dose. Still more preferably, the second dose is administered between 17 and 30 days after the first dose. Even more preferably, the second dose is administered at least 19 days after the first dose. Still more preferably, the second dose is administered between 19 and 25 days after the first dose. Most preferably the second dose is administered at least 21 days after the first dose. In a preferred aspect of the two-time administration regimen, both the first and second doses of the immunogenic composition are administered in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

In another aspect of the present invention said immunogenic composition is administered intranasal.

The immunogenic composition is, preferably, administered topically or systemically. Suitable routes of administration conventionally used are oral or parenteral administration, such as intranasal, intravenous, intramuscular, intraperitoneal, subcutaneous, as well as inhalation. However, depending on the nature and mode of action of a compound, the immunogenic composition may be administered by other routes as well. However, most preferred the immunogenic composition is administered intranasal.

In one aspect of the present invention the subject is Swine influenza virus maternal antibody negative.

It is in the general knowledge of a person skilled in the art how to measure the maternally derived anti-SIV antibodies.

In one aspect of the present invention the immunogenic composition is administered to sows during pregnancy and lactation.

Advantageously, the experimental data provided by the present invention disclose effectiveness and safety of the immunogenic composition in pregnant sows.

Thus, there is provided a method of vaccinating pigs against SIV by administering the SIV vaccine according to the present invention to a pregnant sow at least one time before farrowing, preferably two times before farrowing and most preferably three times prior to farrowing ("repeated doses"). However, preferably, the pregnant sow is vaccinated with the SIV vaccine according to the present invention once with a single dose of said vaccine before farrowing. However, when the vaccine is administered to the sow three times, the first administration should occur between 50 and 60 days before farrowing, preferably between 52 and 58 days before farrowing, and most preferably between 54 and 56 days before farrowing. The second administration should occur between 30 and 40 days before farrowing, preferably between 32 and 38 days before farrowing, and most preferably between 34 and 36 days before farrowing. The final administration should occur between 10 and 20 days before farrowing, preferably between 12 and 18 days before farrowing, and most preferably between 14 and 16 days before farrowing.

It was further discovered that maternal immunity, unexpectedly, does not interfere with successful vaccination of the piglets shortly after birth, and in fact, piglets vaccinated within about one month after birth, as described herein, have reduced clinical signs associated with the disease compared to non-vaccinated piglets. In particular, no interference with successful vaccination of the piglets have been shown when piglets have been vaccinated within the first three weeks of age, within the first week of age, with one day of age and within the first 24 h of age.

In one aspect of the present invention the immunogenic composition is administered to pigs within the first month of age.

Preferably, the pigs to be immunized is between 1 day of age to 40 days of age, 1 day of age to 30 days of age, 1 day of age to 21 days of age, more preferably, said subject to be immunized is between 1 day of age to 10 days of age, even more preferably, between 1 day of age to 9 days of age, even more preferably between 1 day of age to 8 days of age, even more preferably between 1 day of age to 7 days of age, even more preferably between 1 day of age to 6 days of age, even more preferably between 1 day of age to 5 days of age, even more preferably between 1 day of age to 4 days of age, even more preferably between 1 day of age to 3 days of age, even more preferably 1 or 2 day(s) of age, and most preferably 1 day of age or 0 days of age.

More preferably, said pig to be immunized is 1, 2, 3, 4, 5, 6, 7, 8, 9, 10, 11, 12, 13, 14, 15, 16, 17, 18, 19, 20 or 21 days of age.

Advantageously, the experimental data provided by the present invention disclose effectiveness of the immunogenic composition in piglets of about 3 weeks of age and younger.

In one aspect of the present invention the immunogenic composition is administered to pigs within the first two weeks of age.

In one aspect of the present invention the immunogenic composition is administered to pigs within the first week of age.

In another aspect of the present invention the immunogenic composition is administered to pigs at day 1 of age.

Advantageously, the experimental data provided by the present invention disclose effectiveness of the immunogenic composition in piglets of day 1 of age.

In another aspect of the present invention the immunogenic composition is administered to pigs within the first 24 h of age.

Advantageously, the experimental data provided by the present invention disclose effectiveness of the immunogenic composition in pigs within the first 24 h of age.

It is to be understood that pigs within the first 24 h of age are 24 h of age or younger. Preferably, said pigs to be immunized are between 1 h of age to 24 h of age, 2 h of age to 24 h of age, 4 h of age to 24 h of age, 6 h to 24 h of age, 8 h to 24 h of age, 10 h to 24 h of age, 12 h to 24 h of age, 14 h to 24 h of age, 16 h to 24 h of age, 18 h to 24 h of age, 20 h to 24 h of age, 22 h to 24 h of age. More preferably, said pig to be immunized is 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h or 24 h of age.

In one aspect of the present invention the subject is Swine influenza virus maternal antibody positive.

It is in the general knowledge of a person skilled in the art how to measure the maternally derived anti-SIV antibodies.

Preferably, the bivalent immunogenic composition of the present invention comprises the modified live H1 virus of swine influenza or the H1N1 SIV of the present invention in amounts of about $10^2$ to about $10^8$ pfu (plaque forming units) per dose, preferably about $10^3$ to about $10^7$ pfu per dose, even more preferably in an amount of about $10^4$ to about $10^7$ pfu per dose, most preferably in an amount of about $10^4$ to about $10^6$ pfu per dose. More preferably, the bivalent immunogenic composition of the present invention comprises the modified live H1 virus of swine influenza or the H1N1 SIV of the present invention in amounts of about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu per dose.

Preferably, the bivalent immunogenic composition of the present invention comprises the modified live H3 virus of swine influenza or the H3N2 SIV of the present invention in amounts of about $10^2$ to about $10^8$ pfu (plaque forming units) per dose, preferably about $10^3$ to about $10^7$ pfu per dose, even more preferably in an amount of about $10^4$ to about $10^7$ pfu per dose, most preferably in an amount of about $10^4$ to about $10^6$ pfu per dose. More preferably, the bivalent immunogenic composition of the present invention comprises the modified live H3 virus of swine influenza or the H3N2 SIV of the present invention in amounts of about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu per dose.

Preferably, the bivalent immunogenic composition of the present invention comprises both the modified live H3 and H1 viruses of swine influenza or the H1N1 and the H3N2 SIV of the present invention together in amounts of about $10^2$ to about $10^8$ pfu (plaque forming units) of each component per dose, preferably about $10^3$ to about $10^7$ pfu of each component per dose, even more preferably in an amount of about $10^4$ to about $10^7$ pfu of each component per dose, most preferably in an amount of about $10^4$ to about $10^6$ pfu of each component per dose. More preferably, the bivalent immunogenic composition of the present invention comprises both the modified live H3 and H1 viruses of swine influenza or the H1N1 and the H3N2 SIV of the present invention together in amounts of about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu of each component per dose.

Preferably, the bivalent immunogenic composition of the present invention comprises the modified live H1 virus of swine influenza or the H1N1 SIV of the present invention in amounts of about 1 to about 10 $\log_{10}$ FAID$_{50}$/ml (fluorescent antibody infectious dose) per dose, preferably about 2 to about 8 $\log_{10}$ FAID$_{50}$/ml per dose, preferably in an amount of about 2 to about 7 $\log_{10}$ FAID$_{50}$/ml per dose, more preferably in an amount of about 2 to about 6 $\log_{10}$ FAID$_{50}$/ml per dose, even more preferably in an amount of about 2 to about 5 $\log_{10}$ FAID$_{50}$/ml per dose, most preferably in an amount of about 2 to about 4 $\log_{10}$ FAID$_{50}$/ml per dose. More preferably, the bivalent immunogenic composition of the present invention comprises the modified live H1 virus of swine influenza or the H1N1 SIV of the present invention in amounts of about 1, 1.5, 2, 2.5, 3, 3.5, 4, 4.5, 5, 5.5, 6, 6.5, 7, 7.5 or $\log_{10}$ FAID$_{50}$/ml per dose.

Preferably, the bivalent immunogenic composition of the present invention comprises the modified live H3 virus of swine influenza or the H3N2 SIV of the present invention in amounts of about 1 to about 10 $\log_{10}$ FAID$_{50}$/ml (fluorescent antibody infectious dose) per dose, preferably about 2 to about 8 $\log_{10}$ FAID$_{50}$/ml per dose, preferably in an amount of about 2 to about 7 $\log_{10}$ FAID$_{50}$/ml per dose, more preferably in an amount of about 2 to about 6 $\log_{10}$ FAID$_{50}$/ml per dose, even more preferably in an amount of about 2 to about 5 $\log_{10}$ FAID$_{50}$/ml per dose, most preferably in an amount of about 2 to about 4 $\log_{10}$ FAID$_{50}$/ml per dose. More preferably, the bivalent immunogenic composition of the present invention comprises the modified live H3 virus of swine influenza or the H3N2 SIV of the present invention in amounts of about 1, 1.5, 2, 2.5, 3, 3.5, 4, 4.5, 5, 5.5, 6, 6.5, 7, 7.5 or $\log_{10}$ FAID$_{50}$/ml per dose.

Preferably, the bivalent immunogenic composition of the present invention comprises both the modified live H3 and H1 viruses of swine influenza or the H1N1 and the H3N2 SIV of the present invention together in amounts of about 1 to about 10 $\log_{10}$ FAID$_{50}$/ml (fluorescent antibody infectious dose) of each component per dose, preferably about 2 to about 8 $\log_{10}$ FAID$_{50}$/ml of each component per dose, preferably in an amount of about 2 to about 7 $\log_{10}$FAID$_{50}$/ml of each component per dose, more preferably in an amount of about 2 to about 6 $\log_{10}$ FAID$_{50}$/ml of each component per dose, even more preferably in an amount of about 2 to about 5 $\log_{10}$ FAID$_{50}$/ml of each component per dose, most preferably in an amount of about 2 to about 4 $\log_{10}$ FAID$_{50}$/ml of each component per dose. More preferably, the bivalent immunogenic composition of the present invention comprises both the modified live H3 and H1 viruses of swine influenza or the H1N1 and the H3N2 of the present invention together in amounts of about 1, 1.5, 2, 2.5, 3, 3.5, 4, 4.5, 5, 5.5, 6, 6.5, 7, 7.5 or $\log_{10}$FAID$_{50}$/ml of each component per dose.

In one aspect of the present invention the immunogenic composition comprises 2 to 8 $\log_{10}$ of the modified live H1 virus of swine influenza and/or 2 to 8 $\log_{10}$ of the modified live H3 virus of swine influenza.

In one aspect of the present invention the immunogenic composition comprises 2 to 6 $\log_{10}$ of the modified live H1 virus of swine influenza and/or 2 to 6 $\log_{10}$ of the modified live H3 virus of swine influenza.

In one aspect of the present invention the immunogenic composition comprises 2 to 4 $\log_{10}$ of the modified live H1 virus of swine influenza and/or 2 to 4 $\log_{10}$ of the modified live H3 virus of swine influenza.

In one aspect of the present invention said method results in an improvement in an efficacy parameter selected from the group consisting of: a reduction in the weight loss, a lower virus load, a reduction in lung lesions, a reduced shedding, a reduced rectal temperature, or combinations thereof, in comparison to a subject of a non-immunized control group of the same species.

The term "reducing", "reduced", "reduction" or "lower" means, that the efficacy parameter (weight loss, virus load, lung lesions, shedding, rectal temperature) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

Advantageously, the experimental data provided by the present invention disclose effectiveness of the immunogenic composition by lowering the virus load, reducing the lung lesions and reducing the shedding.

In one aspect of the present invention said method results in an improvement in an efficacy parameter selected from the group consisting of: a reduction in the weight loss, a lower virus load, a reduction in lung lesions, a reduced shedding, a reduced rectal temperature, or combinations thereof, in comparison to a subject of the same species immunized with a monovalent modified live H3 or H1 virus of swine influenza.

The term "virus load" is well known to the person skilled in that art. The term virus load is interchangeable used with the term viral titer herein. The virus load or virus titer is a measure of the severity of an active viral infection, and can be determined by methods known to the person skilled in the art. The determination can be based on the detection of viral proteins such as by antibody binding to the viral proteins and further detection or, alternatively, by detection of viral nucleic acids by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma.

In one aspect of the present invention the monovalent modified live H3 or H1 virus of swine influenza is a H1N1 NS1 deletion mutant of swine influenza virus.

In one aspect of the present invention the monovalent modified live H3 or H1 virus of swine influenza is the H1N1 NS1 deletion mutant of swine influenza virus as described herein.

In one aspect of the present invention the monovalent modified live H3 or H1 virus of swine influenza is a H3N2 NS1 deletion mutant of swine influenza virus.

In one aspect of the present invention the monovalent modified live H3 or H1 virus of swine influenza is the H3N2 NS1 deletion mutant of swine influenza virus as described herein.

In one aspect of the present invention the treatment or prophylaxis results in shortening of the virus load phase as compared to animals of a non-treated control group of the same species.

In one aspect of the present invention the treatment or prophylaxis results in a reduction of the shedding from day 5 after challenge or infection.

In another aspect of the present invention the treatment or prophylaxis results in a reduction of the shedding from day 1 after challenge or infection.

In another aspect of the present invention the treatment or prophylaxis results in a reduction of the shedding from day 2 after challenge or infection.

Advantageously, the experimental data provided by the present invention disclose a reduced shedding of the SIV virus after challenge in pigs that have received the immunogenic composition described herein.

Preferably, the shedding of the SIV virus is reduced from day 5 after challenge or infection, more preferably from day 4 after challenge or infection, more preferably from day 3 after challenge or infection and most preferably from day 1 or 2 after challenge or infection with the SIV as compared to a subject of a non-immunized control group of the same species.

The term "reduction of the shedding" means, that the shedding is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the reduction of the shedding.

In one aspect of the present invention the subject is immunized with a lower concentration of the immunogenic composition as described herein compared to a subject of the same species immunized with a monovalent modified live H3 or H1 virus of swine influenza.

The term "lower concentration" means, that the concentration of the modified live H3 and H1 virus of swine influenza or the H1N1 and H3N2 NS1 deletion mutants of Swine Influenza virus as described herein in the bivalent immunogenic composition of the present invention is reduced approximately 1 to approximately 100 fold, approximately 5 to approximately 80 fold or approximately 20 to approximately 80 fold, or 1, 2, 3, 4, 5, 7, 10, 15, 20, 25, 30, 35, 40, 45, 50, 55, 60, 65, 70, 72, 75, 80, 85, 90, 95 or 100 fold when compared to a monovalent modified live H3 or H1 virus of swine influenza or monovalent NS1 deletion mutant of swine influenza virus. It is in the general knowledge of a person skilled in the art how to measure the concentration of a virus. Examples are the plague forming unit assay, the focus forming assay, endpoint dilution assays (such as TCID50 or FAID50), protein assays, hemagglutination assays, bicinchoninic acid assay, single radial immunodiffusion assay, transmission electron microscopy, tunable resistive pulse sensing, flow cytometry, quantitative polymerase chain reaction, enzyme-linked immunosorbent assays and the alike.

Preferably, the bivalent immunogenic composition of the present invention comprises each the modified live H3 and H1 viruses of swine influenza or the H1N1 NS1 and H3N2 NS1 deletion mutant of SIV of the present invention in amounts of about 1 to about 4 $\log_{20}$ FAID$_{50}$/ml (fluorescent antibody infectious dose) per dose, about 2 to about 4 $\log_{10}$ FAID$_{50}$/ml per dose, most preferably about 2 to about 3 $\log_{10}$FAID$_{50}$/ml per dose.

The bivalent immunogenic composition described herein is a synergistic combination comprising i) the modified live H1 virus of swine influenza or the H1N1 NS1 deletion mutant of Swine Influenza virus as described herein and ii) the modified live H3 virus of swine influenza or the H3N2 NS1 deletion mutant of swine influenza virus as described herein in an amount effective to induce protection in a subject to subsequent challenge by a virulent SIV strain. In particular, lower concentrations of the bivalent immunogenic composition as described herein are needed to induce protection in a subject compared to an immunogenic composition comprising a monovalent modified live H3 or H1 virus of swine influenza or a NS1 deletion mutant of swine influenza virus only. Thus, the bivalent vaccine comprising the modified live H3 and H1 viruses of swine influenza or the H1N1 NS1 and H3N2 NS1 deletion mutant of swine influenza virus produce greater protection than monovalent modified live H3 or H1 viruses of swine influenza or NS1 deletion mutant of swine influenza virus.

In one aspect of the present invention the modified live H3 and H1 viruses of swine influenza act synergistically together.

In one aspect of the present invention the concentration of the modified live H3 and H1 viruses of swine influenza are reduced compared to the concentration of the H3 virus of swine influenza in a monovalent immunogenic composition and the concentration of the H1 virus of swine influenza in a monovalent immunogenic composition.

In one aspect of the present invention the modified live H3 virus of swine influenza increases the protection against a heterologous challenge, provides a cross-protection effect.

In one aspect of the present invention the modified live H3 virus of swine influenza increases the protection against a H1 challenge.

In one aspect of the present invention the modified live H3 virus of swine influenza increases the protection against a H1N1 challenge.

In one aspect of the present invention the modified live H3 virus of swine influenza is a H3N2 NS1 deletion mutant of swine influenza virus.

In one aspect of the present invention the monovalent modified live H3 virus of swine influenza is the H3N2 NS1 deletion mutant of swine influenza virus as described herein.

The experimental data provided herein show that a combination of the modified live H3 and H1 viruses of swine influenza or the H1N1 NS1 and H3N2 deletion mutant of swine influenza virus together is, surprisingly more potent than the aggregate effect of the individual components.

The synergistic effect of the bivalent vaccine of the present invention is very clearly demonstrated by its ability to provide protection when administered at a much lower inclusion level than what is required for the monovalent H1N1 vaccine. The bivalent vaccine of the present invention administered at a total dose of only 3.13 $\log_{10}FAID_{50}$/mL provided protection as compared to the monovalent vaccine which showed a similar level of protection after being administered at a dose of 4.99 $\log_{10}FAID_{50}$/mL (about 72-times more than the total dose of bivalent vaccine). Further, Vincent et al 2012 (Journal of Virology 19: 10597 to 10605) have shown that $1\times10^6$ $TCID_{50}$ (correspond to 6 $\log_{10}$ $FAID_{50}$) of the monovalent H3N2 provided protection (about 741-times more than the total dose of bivalent vaccine). Thus, the concentration of the H1 and H3 components in the bivalent vaccine are dramatically reduced compared to the concentrations needed in the monovalent vaccines. This is an unexpected surprising synergistic effect.

There is even further supporting evidence of the synergistic effect of the bivalent vaccine when the amount of challenge virus is considered. The monovalent vaccine even administered at the higher dose provided only a similar level of protection from a challenge of approximately 3-times less of the same challenge isolate.

The conclusion made from the data generated in these studies is that there are reductions in the amount of virus shed from the nasal passages, there are reductions in the virus isolation positive lungs as well as reductions in the primary efficacy parameter of gross lung lesions, at much lower doses of antigen when the vaccine is administered as a bivalent product as compared to when it is administered as a monovalent product. All taken together the data indicates that a single intranasal dose of the bivalent vaccine is more efficacious than the higher dose monovalent vaccine used in naïve pigs in these studies.

The synergistic combination of the present invention is advantageous since the chances of adverse effects are reduced. Additionally, a bivalent vaccine containing a lower concentration than the individual components will clearly be easier and cheaper to manufacture as well.

Moreover, there is a further advantageous surprising synergistic effect besides the above described synergistic concentration effect. The H3 component synergistically acts with the H1 component. The synergistic effect of the bivalent vaccine is very clearly demonstrated by its ability to provide protection from the heterologous H1N2 (A/Swine/North Carolina/001169/2006) SIV isolate. Thus, there is a cross protection effect. This effect is, further, synergistic because the bivalent vaccine of the present invention is administered at a much lower inclusion level than what is required for the monovalent vaccines as described above.

In one aspect of the present invention the monovalent NS1 deletion mutant of swine influenza virus is a H1N1 NS1 deletion mutant of swine influenza virus.

In one aspect of the present invention the monovalent NS1 deletion mutant of swine influenza virus is the H1N1 NS1 deletion mutant of swine influenza virus as described herein.

In one aspect of the present invention the monovalent NS1 deletion mutant of swine influenza virus is a H3N2 NS1 deletion mutant of swine influenza virus.

In one aspect of the present invention the monovalent NS1 deletion mutant of swine influenza virus is the H3N2 NS1 deletion mutant of swine influenza virus as described herein.

The present invention also relates to the use of the immunogenic composition as described herein for the treatment and/or prophylaxis of swine influenza virus infections in a subject.

The present invention also relates to the use of the immunogenic composition as described herein for the manufacture of a medicament.

The present invention also relates to the immunogenic composition as described herein for use as a medicament.

The present invention also relates to the immunogenic composition as described herein for use in a method for the treatment and/or prophylaxis of swine influenza virus infections in a subject.

DETAILED DESCRIPTION

The invention provides the following exemplary embodiments:

An immunogenic composition comprising: a) a modified live H3 virus of swine influenza, and b) a modified live H1 virus of swine influenza.

The immunogenic composition comprising the above embodiment, wherein the modified live H3 and H1 viruses of swine influenza have a N (neuraminidase) subtype selected from the group consisting of N1, N2, N3, N4, N5, N6, N7, N8, N9 and N10.

The immunogenic composition comprising any of the preceding embodiments, wherein the modified live H3 virus of swine influenza is H3N2 of swine influenza and/or the modified live H1 virus of swine influenza is H1N1 of swine influenza virus.

The immunogenic composition comprising any of the preceding embodiments, wherein the modified live H3 and H1 viruses of swine influenza have one or more mutations in the NS1 gene.

The immunogenic composition comprising any of the preceding embodiments, wherein the modified live H3 and H1 viruses of swine influenza have a deletion within the NS1 gene.

The immunogenic composition comprising any of the preceding embodiments, wherein the modified live H3 and H1 viruses of swine influenza are attenuated swine influenza viruses.

The immunogenic composition comprising any of the preceding embodiments, wherein the modified live H3 and H1 viruses of swine influenza are mutagenized viruses or reassortants.

The immunogenic composition comprising any of the preceding embodiments, wherein the modified live H3 and H1 viruses of swine influenza are genetically engineered.

The immunogenic composition comprising any of the preceding embodiments, wherein the modified live H3 and H1 viruses of swine influenza have an impaired interferon antagonist phenotype.

The immunogenic composition comprising any of the preceding embodiments, wherein the modified live H3 and H1 viruses of swine influenza have one or more mutations at the carboxy terminus of the NS1 protein.

The immunogenic composition comprising any of the preceding embodiments, wherein the modified live H3 and H1 viruses of swine influenza have a carboxy-terminal truncated NS1 protein.

The immunogenic composition comprising any of the preceding embodiments, wherein the modified live H3 and H1 viruses of swine influenza have a carboxy-terminal truncated NS1 protein comprising NS1 amino acids 1 through 124, 1 through 125, 1 through 126, 1 through 127 or 1 through 128, wherein the amino terminal amino acid is number 1

The immunogenic composition comprising any of the preceding embodiments, wherein the modified live H3 and H1 viruses of swine influenza have a carboxy-terminal truncated NS1 protein comprising NS1 amino acids 1 through 126.

The immunogenic composition comprising any of the preceding embodiments, NS1 protein resulting in a deletion of 91, 92, 93 or 94 amino acid residues from the carboxy terminus of NS1.

The immunogenic composition comprising any of the preceding embodiments, wherein the modified live H3 and H1 viruses of swine influenza have a NS1 gene or protein from A/Swine/Texas/4199-2/98.

The immunogenic composition comprising any of the preceding embodiments, wherein the modified live H3 virus of swine influenza encodes a carboxy-terminal truncated NS1 protein comprising NS1 amino acids 1 through 124, 1 through 125, 1 through 126, 1 through 127 or 1 through 128, wherein the amino terminal amino acid is number 1.

The immunogenic composition comprising any of the preceding embodiments, wherein the modified live H3 virus of swine influenza encodes a carboxy-terminal truncated NS1 protein comprising NS1 amino acids 1 through 126, wherein the amino terminal amino acid is number 1.

The immunogenic composition comprising any of the preceding embodiments, NS1 protein resulting in a deletion of 91, 92, 93 or 94 amino acid residues from the carboxy terminus of NS1.

The immunogenic composition comprising any of the preceding embodiments, wherein the modified live H3 virus of swine influenza is A/Swine/Texas/4199-2/98.

The immunogenic composition comprising any of the preceding embodiments, wherein the modified live H3 virus of swine influenza is TX/98/del 126.

The immunogenic composition comprising any of the preceding embodiments, wherein the modified live H3 virus of swine influenza contains the HA, NA, PB2, PB1, PA, NP, and M from A/Swine/Texas/4199-2/98 and the NS1-126 gene is from A/Swine/Texas/4199-2/98.

The immunogenic composition comprising any of the preceding embodiments, wherein the modified live H3 virus of swine influenza a) comprises a nucleic acid sequence of gene segments having the NA and HA genes whose cDNA has at least 70% identity to the nucleic acid sequence as set forth in SEQ ID NO:1 or SEQ ID NO:2, or b) comprises a nucleic acid sequence of gene segments having the NA and HA genes encoding NA and HA proteins having an amino acid sequence with at least 70% identity to the amino acid sequence as set forth in SEQ ID NO:3 or SEQ ID NO:4, or c) comprises a NA and HA protein having an amino acid sequence with at least 70% identity to the amino acid sequence as set forth in SEQ ID NO:3 or SEQ ID NO:4.

The H1N1 NS1 deletion mutant of Swine Influenza virus of any one of preceding embodiments, wherein the modified live H3 virus of swine influenza a) comprises a nucleic acid sequences of gene segments having the NA and HA genes whose cDNA has at least 70%, at least 75%, at least 80%, at least 85%, at least 90%, at least 91%, at least 92%, at least 93%, at least 94%, at least 95%, at least 96%, at least 97%, at least 98% or at least 99% identity to the nucleic acid sequence as set forth in SEQ ID NO:5 or SEQ ID NO:6, or b) comprises a nucleic sequences of gene segments having the NA and HA genes encoding NA and HA proteins having amino acid sequences with at least 70%, at least 75%, at least 80%, at least 85%, at least 90%, least 91%, at least 92%, at least 93%, at least 94%, at least 95%, at least 96%, at least 97%, at least 98% or at least 99% identity to the amino acid sequence as set forth in SEQ ID NO:7 or SEQ ID NO:8, or c) comprises a NA and HA protein having an amino acid sequence with at least 70%, at least 75%, at least 80%, at least 85%, at least 90%, at least 91%, at least 92%, at least 93%, at least 94%, at least 95%, at least 96%, at least 97%, at least 98% or at least 99% identity the amino acid sequence as set forth in SEQ ID NO:7 or SEQ ID NO:8.

The immunogenic composition comprising any of the preceding embodiments, wherein the modified live H1 virus of swine influenza is a chimeric virus.

The immunogenic composition comprising any of the preceding embodiments, wherein the modified live H1 virus of swine influenza comprises a carboxy-terminal truncated NS1 of a H3 SIV strain, preferably a carboxy-terminal truncated NS1 of a H3N2 SIV strain.

The immunogenic composition comprising any of the preceding embodiments, wherein the modified live H1 virus of swine influenza encodes a carboxy-terminal truncated NS1 protein comprising NS1 amino acids 1 through 124, 1 through 125, 1 through 126, 1 through 127 or 1 through 128, wherein the amino terminal amino acid is number 1.

The immunogenic composition comprising any of the preceding embodiments, wherein the modified live H1 virus of swine influenza encodes a carboxy-terminal truncated NS1 protein comprising NS1 amino acids 1 through 126, wherein the amino terminal amino acid is number 1.

The immunogenic composition comprising any of the preceding embodiments, wherein the modified live H1 virus of swine influenza encodes a carboxy-terminal truncated NS1 protein resulting in a deletion of 91, 92, 93 or 94 amino acid residues from the carboxy terminus of NS1.

The immunogenic composition comprising any of the preceding embodiments, wherein the modified live H1 virus of swine influenza is A/Swine/Texas/4199-2/98.

The immunogenic composition comprising any of the preceding embodiments, wherein the modified live H1 virus of swine influenza comprises the hemagglutinin and neuraminidase gene segments from a H1N1 subtype.

The immunogenic composition comprising any of the preceding embodiments, wherein the modified live H1 virus of swine influenza comprises the hemagglutinin and neuraminidase gene segments from A/swine/Minnesota/37866/1999.

The immunogenic composition comprising any of the preceding embodiments, wherein the modified live H1 virus of swine influenza contains HA and NA from A/swine/Minnesota/37866/1999 (H1N1) and PB2, PB1, PA, NP, M from A/Swine/Texas/4199-2/98 (H3N2) and the NS1-126 gene is from A/Swine/Texas/4199-2/98 (H3N2).

The immunogenic composition comprising any of the preceding embodiments, wherein the modified live H1 virus of swine influenza is a chimeric of A/swine/Minnesota/37866/1999 and TX/98/del 126.

The immunogenic composition comprising any of the preceding embodiments, wherein the modified live H1 virus of swine influenza a) comprises a nucleic acid sequence of gene segments having the NA and HA genes whose cDNA has greater than 70% identity to the nucleic acid sequence as set forth in SEQ ID NO:5 or SEQ ID NO:6, or b) comprises a nucleic sequence of gene segments having the NA and HA genes encoding NA and HA proteins having an amino acid sequence with greater than 70% identity to the amino acid sequence as set forth in SEQ ID NO:7 or SEQ ID NO:8, or c) comprises a NA and HA protein having an amino acid sequence with greater than 70% identity to the amino acid sequence as set forth in SEQ ID NO:7 or SEQ ID NO:8.

The H1N1 NS1 deletion mutant of Swine Influenza virus of any one of preceding embodiments, wherein the modified live H1 virus of swine influenza a) comprises a nucleic acid sequences of gene segments having the NA and HA genes whose cDNA has at least 70%, at least 75%, at least 80%, at least 85%, at least 90%, at least 91%, at least 92%, at least 93%, at least 94%, at least 95%, at least 96%, at least 97%, at least 98% or at least 99% identity to the nucleic acid sequence as set forth in SEQ ID NO:5 or SEQ ID NO:6, or b) comprises a nucleic sequences of gene segments having the NA and HA genes encoding NA and HA proteins having amino acid sequences with at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:7 or SEQ ID NO:8, or c) comprises a NA and HA protein having an amino acid sequence with at least 70%, at least 75%, at least 80%, at least 85%, at least 90%, at least 91%, at least 92%, at least 93%, at least 94%, at least 95%, at least 96%, at least 97%, at least 98% or at least 99% identity the amino acid sequence as set forth in SEQ ID NO:7 or SEQ ID NO:8.

The immunogenic composition comprising any of the preceding embodiments, wherein said immunogenic composition is formulated for a single-dose administration.

The immunogenic composition comprising any of the preceding embodiments, wherein said immunogenic composition is administered intranasal.

The immunogenic composition comprising any of the preceding embodiments, wherein the immunogenic composition is safe for sows during pregnancy and lactation.

The immunogenic composition comprising any of the preceding embodiments, wherein the immunogenic composition is safe for pigs within the first two weeks of age, preferably within the first week of age.

The immunogenic composition comprising any of the preceding embodiments, wherein the immunogenic composition is safe for pigs at day 0 of age.

The immunogenic composition comprising any of the preceding embodiments, wherein said immunogenic composition further comprises a pharmaceutically acceptable carrier.

The immunogenic composition comprising any of the preceding embodiments, wherein the immunogenic composition comprises 2 to 8 log 10 of the modified live H1 virus of swine influenza and/or 2 to 8 log 10 of the modified live H3 virus of swine influenza.

The immunogenic composition comprising any of the preceding embodiments, wherein the immunogenic composition comprises 2 to 6 log 10 of the modified live H1 virus of swine influenza and/or 2 to 6 log 10 of the modified live H3 virus of swine influenza.

The immunogenic composition comprising any of the preceding embodiments, wherein the immunogenic composition comprises 2 to 4 log 10 of the modified live H1 virus of swine influenza and/or 2 to 4 log 10 of the modified live H3 virus of swine influenza.

The immunogenic composition comprising any of the preceding embodiments, wherein said immunogenic composition is a vaccine.

The immunogenic composition comprising any of the preceding embodiments, wherein said immunogenic composition is a bivalent vaccine.

The immunogenic composition comprising any of the preceding embodiments, wherein the immunogenic composition is effective in the treatment and/or prophylaxis of clinical signs caused by SIV in a subject of need.

The immunogenic composition comprising any of the preceding embodiments, wherein the modified live H3 and H1 viruses of swine influenza act synergistically together.

The immunogenic composition comprising any of the preceding embodiments, wherein the concentration of the modified live H3 and H1 viruses of swine influenza are reduced compared to the concentration of the H3 virus of swine influenza in a monovalent immunogenic composition and the concentration of the H1 virus of swine influenza in a monovalent immunogenic composition.

The immunogenic composition comprising any of the preceding embodiments, wherein the modified live H3 virus of swine influenza increases the protection against a heterologous challenge.

The immunogenic composition comprising any of the preceding embodiments, wherein the modified live H3 virus of swine influenza increases the protection against a H1 challenge.

The immunogenic composition comprising any of the preceding embodiments, wherein the modified live H3 virus of swine influenza increases the protection against a H1N1 challenge.

A method for immunizing a subject comprising administering to such subject an immunogenic composition of any one of the preceding embodiments.

A method of treating or preventing clinical signs caused by swine influenza virus in a subject of need, the method comprising administering to the subject a therapeutically effective amount of an immunogenic composition according to any one of the preceding embodiments.

A method of reducing the viral shedding in a subject of need, in comparison to a subject of a non-immunized control group of the same species, the method comprising administering to the subject a therapeutically effective amount of an immunogenic composition according to any one of the preceding embodiments.

A method of reducing the viral shedding in a subject of need, in comparison to a subject of an immunized control group of the same species immunized with a monovalent modified live H3 or H1 virus of swine influenza, the method comprising administering to the subject a therapeutically effective amount of an immunogenic composition according to any one of the preceding embodiments.

A method of vaccinating a subject having anti-SIV antibodies comprising the step of administering to said animal a single effective dose of an immunogenic composition according to any one of the preceding embodiments.

A method for preventing or reducing early SIV infections in a subject, the method comprising administering to the subject a therapeutically effective amount of an immunogenic composition according to any one of the preceding embodiments.

The method according to any one of the preceding methods, wherein said subject is selected from the group consisting of swine, cattle, cat and dog.

The method according to any one of the preceding methods, wherein the immunogenic composition is administered once.

The method according to any one of the preceding methods, wherein the immunogenic composition is administered at two or more doses.

The method according to any one of the preceding methods, wherein said immunogenic composition is administered intranasal.

A method according to any one of the preceding methods, wherein the subject is Swine influenza virus maternal antibody negative.

The method according to any one of the preceding methods, wherein said immunogenic composition is administered to sows during pregnancy and lactation.

The method according to any one of the preceding methods, wherein the immunogenic composition is administered to pigs within the first month of age.

The method according to any one of the preceding methods, wherein the immunogenic composition is administered to pigs within the first two weeks of age, preferably within the first week of age.

The method according to any one of the preceding methods, wherein the immunogenic composition is administered to pigs at day 1 of age.

The method according to any one of the preceding embodiments, wherein the immunogenic composition is administered to pigs within the first 24 h of age.

The method according to the any one of the preceding methods, wherein the subject is Swine influenza virus maternal antibody positive.

The method according to any one of the preceding methods, wherein the immunogenic composition comprises 2 to 8 log 10 of the modified live H1 virus of swine influenza and/or 2 to 8 log 10 of the modified live H3 virus of swine influenza.

The method according to any one of the preceding methods, wherein the immunogenic composition comprises 2 to 6 log 10 of the modified live H1 virus of swine influenza and/or 2 to 6 log 10 of the modified live H3 virus of swine influenza.

The method according to any one of the preceding methods, wherein the immunogenic composition comprises 2 to 4 log 10 of the modified live H1 virus of swine influenza and/or 2 to 4 log 10 of the modified live H3 virus of swine influenza.

The method according to any one of the preceding methods, wherein said method results in an improvement in an efficacy parameter selected from the group consisting of: a reduction in weight loss, a lower virus load, a reduction in lung lesions, a reduced shedding, a reduced rectal temperature, or combinations thereof, in comparison to a subject of a non-immunized control group of the same species.

The method according to any one of the preceding methods, wherein said method results in an improvement in an efficacy parameter selected from the group consisting of: a reduction in the weight loss, a lower virus load, a reduction in lung lesions, a reduced shedding, a reduced rectal temperature, or combinations thereof, in comparison to a subject of the same species immunized with a monovalent modified live H3 or H1 virus of swine influenza.

The method according to any one of the preceding methods, wherein the treatment or prophylaxis results in shortening of the virus load phase as compared to animals of a non-treated control group of the same species.

The method according to any one of the preceding wherein the treatment or prophylaxis results in a reduction of the shedding from day 5 after challenge or infection.

The method according to any one of the preceding methods, wherein the treatment or prophylaxis results in a reduction of the shedding from day 1 or day 2 after challenge or infection.

The method according to any one of the preceding methods, wherein the subject is immunized with a lower concentration of the immunogenic composition of any one of the preceding embodiments compared to a subject of the same species immunized with a monovalent modified live H3 or H1 virus of swine influenza.

The method according to any one of the preceding methods, wherein the monovalent modified live H3 or H1 virus of swine influenza is a H1N1 NS1 deletion mutant of swine influenza virus.

The method according to the above embodiment, wherein the H1N1 NS1 deletion mutant of swine influenza virus is the H1N1 NS1 deletion mutant of swine influenza virus comprising any one of the preceding embodiments.

The method according to any one of the preceding embodiments, wherein the monovalent modified live H3 or H1 virus of swine influenza is a H3N2 NS1 deletion mutant of swine influenza virus.

The method according to the above embodiment, wherein the H3N2 NS1 deletion mutant of swine influenza virus is the H3N2 NS1 deletion mutant of swine influenza virus comprising any one of the preceding embodiments.

The method according to any one of the preceding embodiments, wherein the modified live H3 and H1 viruses of swine influenza act synergistically together.

The method according to any one of the preceding embodiments, wherein the concentration of the modified live H3 and H1 viruses of swine influenza are reduced compared to the concentration of the H3 virus of swine influenza in a monovalent immunogenic composition and the concentration of the H1 virus of swine influenza in a monovalent immunogenic composition.

The method according to any one of the preceding embodiments, wherein the modified live H3 virus of swine influenza increases the protection against a heterologous challenge.

The method according to any one of the preceding embodiments, wherein the modified live H3 virus of swine influenza increases the protection against a H1 challenge.

The method according to any one of the preceding embodiments, wherein the modified live H3 virus of swine influenza increases the protection against a H1N1 challenge.

An immunogenic composition comprising any one of the preceding embodiments for use in a method for immunizing a subject comprising administering said immunogenic composition to such subject.

The immunogenic composition comprising any one of the preceding embodiments for use in a method of treating or preventing clinical signs caused by swine influenza virus in a subject of need, the method comprising administering to the subject a therapeutically effective amount of said immunogenic composition.

The immunogenic composition comprising any one of the preceding embodiments for use in a method of reducing the viral shedding in a subject of need, in comparison to a subject of a non-immunized control group of the same species, the method comprising administering to the subject a therapeutically effective amount of said immunogenic composition.

The immunogenic composition comprising any one of the preceding embodiments for use in a method of reducing the viral shedding in a subject of need, in comparison to a subject of an immunized control group of the same species immunized with a monovalent modified live H3 or H1 virus of swine influenza, the method comprising administering to the subject a therapeutically effective amount of said immunogenic composition.

The immunogenic composition comprising any one of the preceding embodiments for use in a method of vaccinating a subject having anti-SIV antibodies comprising the step of administering to said animal a single effective dose of said immunogenic composition.

The immunogenic composition comprising any one of the preceding embodiments for use in a method for preventing or reducing early SIV infections in a subject, the method comprising administering to the subject a therapeutically effective amount of said immunogenic composition.

The immunogenic composition comprising any one of the preceding embodiments for use according to any one of the preceding methods, wherein said subject is selected from the list consisting of swine, cattle, cat and dog.

The immunogenic composition comprising any one of the preceding embodiments for use according to any one of the preceding methods, wherein the immunogenic composition is administered once.

The immunogenic composition comprising any one of the preceding embodiments for use according to of any one of the preceding methods, wherein the immunogenic composition is administered at two or more doses.

The immunogenic composition comprising any one of the preceding embodiments for use according to any one of the preceding methods, wherein said immunogenic composition is administered intranasal.

The immunogenic composition comprising any one of the preceding embodiments for use according to any one of the preceding methods, wherein the subject is Swine influenza virus maternal antibody negative.

The immunogenic composition comprising any one of the preceding embodiments or use according to of any one of the preceding methods, wherein said immunogenic composition is administered to sows during pregnancy and lactation.

The immunogenic composition comprising any one of the preceding embodiments for use according to of any one of the preceding methods, wherein the immunogenic composition is administered to pigs within the first month of age.

The immunogenic composition comprising any one of the preceding embodiments for use according to any one of the preceding methods, wherein the immunogenic composition is administered to pigs within the first two weeks of age, preferably within the first week of age.

The immunogenic composition comprising any one of the preceding embodiments for use according to any one of the preceding methods, wherein the immunogenic composition is administered to pigs at day 1 of age.

The immunogenic composition comprising any one of the preceding embodiments for use according to any one of the preceding methods, wherein the immunogenic composition is administered to pigs within the first 24 h of age.

The immunogenic composition comprising any one of the preceding embodiments for use according to any one of the preceding methods, wherein the subject is Swine influenza virus maternal antibody positive.

The immunogenic composition comprising any one of the preceding embodiments for use according to any one of the preceding methods, wherein the immunogenic composition comprises 2 to 8 log 10 of the modified live H1 virus of swine influenza and/or 2 to 8 log 10 of the modified live H3 virus of swine influenza.

The immunogenic composition comprising any one of the preceding embodiments for use according to any one of the preceding methods, wherein the immunogenic composition comprises 2 to 6 log 10 of the modified live H1 virus of swine influenza and/or 2 to 6 log 10 of the modified live H3 virus of swine influenza.

The immunogenic composition comprising any one of the preceding embodiments for use according to any one of the preceding methods, wherein the immunogenic composition comprises 2 to 4 log 10 of the modified live H1 virus of swine influenza and/or 2 to 4 log 10 of the modified live H3 virus of swine influenza.

The immunogenic composition comprising any one of the preceding embodiments for use according to any one of the preceding methods, wherein said method results in an improvement in an efficacy parameter selected from the group consisting of: a reduction in weight loss, a lower virus load, a reduction in lung lesions, a reduced shedding, a reduced rectal temperature, or combinations thereof, in comparison to a subject of a non-immunized control group of the same species.

The immunogenic composition comprising any one of the preceding embodiments for use according to any one of the preceding methods, wherein said method results in an improvement in an efficacy parameter selected from the group consisting of: a reduction in weight loss, a lower virus load, a reduction in lung lesions, a reduced shedding, a reduced rectal temperature, or combinations thereof, in comparison to a subject of the same species immunized with a monovalent modified live H3 or H1 virus of swine influenza.

The immunogenic composition comprising any one of the preceding embodiments for use according to any one of the preceding methods, wherein the treatment or prophylaxis results in shortening of the virus load phase as compared to animals of a non-treated control group of the same species.

The immunogenic composition comprising any one of the preceding embodiments for use according to any one of the preceding methods, wherein the treatment or prophylaxis results in a reduction of the shedding from day 5 after challenge or infection.

The immunogenic composition comprising any one of the preceding embodiments for use according to any one of the preceding methods, wherein the treatment or prophylaxis results in a reduction of the shedding from day 1 or day 2 after challenge or infection.

The immunogenic composition comprising any one of the preceding embodiments for use according to any one of the preceding embodiments, wherein the subject is immunized with a lower concentration of the immunogenic composition of any one of the preceding embodiments compared to a subject of the same species immunized with a monovalent modified live H3 or H1 virus of swine influenza.

The immunogenic composition comprising any one of the preceding embodiments for use according to any one of the preceding methods, wherein the monovalent modified live H3 or H1 virus of swine influenza is a H1N1 NS1 deletion mutant of swine influenza virus.

The immunogenic composition for use according to the above embodiment, wherein the H1N1 NS1 deletion mutant of swine influenza virus is the H1N1 NS1 deletion mutant of swine influenza virus according to any one of the preceding embodiments.

The immunogenic composition comprising any one of the preceding embodiments for use according to any one of preceding methods, wherein the monovalent modified live H3 or H1 virus of swine influenza is a H3N2 NS1 deletion mutant of swine influenza virus.

The immunogenic composition for use according to the above embodiment, wherein the H3N2 NS1 deletion mutant of swine influenza virus is the H3N2 NS1 deletion mutant of swine influenza virus according to any one of the preceding embodiments.

The immunogenic composition comprising any one of the preceding embodiments for use according to any one of the preceding methods, wherein the modified live H3 and H1 viruses of swine influenza act synergistically together.

The immunogenic composition comprising any one of the preceding embodiments for use according to any one of the preceding methods, wherein the concentration of the modified live H3 and H1 viruses of swine influenza are reduced compared to the concentration of the H3 virus of swine influenza in a monovalent immunogenic composition and the concentration of the H1 virus of swine influenza in a monovalent immunogenic composition.

The immunogenic composition comprising any one of the preceding embodiments for use according to any one of the preceding methods, wherein the modified live H3 virus of swine influenza increases the protection against a heterologous challenge.

The immunogenic composition comprising any one of the preceding embodiments for use according to any one of the preceding methods, wherein the modified live H3 virus of swine influenza increases the protection against a H1 challenge.

The immunogenic composition comprising any one of the preceding embodiments for use according to any one of the preceding methods, wherein the modified live H3 virus of swine influenza increases the protection against a H1N1 challenge.

The immunogenic composition according to any one of the preceding embodiments for use as a medicament.

The use of an immunogenic composition comprising any one of the preceding embodiments for the treatment and/or prophylaxis of swine influenza virus infections in a subject.

The use of the immunogenic composition comprising any one of the preceding embodiments for the manufacture of a medicament.

A modified live H1 virus of swine influenza.

A modified live H1 virus of swine influenza, wherein the modified live H1 virus of swine influenza has a N (neuraminidase) subtype selected from the group consisting of N1, N2, N3, N4, N5, N6, N7, N8, N9 and N10.

The modified live H1 virus of swine influenza comprising any one of the preceding embodiments, wherein the modified live H1 virus of swine influenza is H1N1 of swine influenza virus.

The modified live H1 virus of swine influenza of any one of the preceding embodiments, wherein the modified live H1 virus of swine influenza has one or more mutations in the NS1 gene.

The modified live H1 virus of swine influenza of any one of the embodiments, wherein the modified live H1 virus of swine influenza has a deletion within the NS1 gene.

The modified live H1 virus of swine influenza of any one of the preceding embodiments, wherein the modified live H1 virus of swine influenza is a chimeric virus.

The modified live H1 virus of swine influenza of any one of the preceding embodiments, wherein the modified live H1 virus of swine influenza comprises a carboxy-terminal truncated NS1 of a H3 SIV strain, preferably a H3N2 SIV strain.

The modified live H1 virus of swine influenza of any one of the preceding embodiments, wherein the modified live H1 virus of swine influenza encodes a carboxy-terminal truncated NS1 protein comprising NS1 amino acids 1 through 124, 1 through 125, 1 through 126, 1 through 127 or 1 through 128, wherein the amino terminal amino acid is number 1.

The modified live H1 virus of swine influenza of any one of the preceding embodiments, wherein the modified live H1 virus of swine influenza encodes a carboxy-terminal truncated NS1 protein comprising NS1 amino acids 1 through 126, wherein the amino terminal amino acid is number 1.

The modified live H1 virus of swine influenza of any one of the preceding embodiments, wherein the modified live H1 virus of swine influenza encodes a carboxy-terminal truncated NS1 protein resulting in a deletion of 91, 92, 93 or 94 amino acid residues from the carboxy terminus of NS1.

The modified live H1 virus of swine influenza of any one of the preceding embodiments, wherein the NS1 gene or protein of the modified live H1 virus of swine influenza is from A/Swine/Texas/4199-2/98.

The modified live H1 virus of swine influenza of any one of the preceding embodiments, wherein the modified live H1 virus of swine influenza comprises the hemagglutinin and neuraminidase gene segments from a H1N1 subtype.

The modified live H1 virus of swine influenza of any one of the preceding embodiments, wherein the modified live H1 virus of swine influenza comprises the hemagglutinin and neuraminidase gene segments from A/swine/Minnesota/37866/1999.

The modified live H1 virus of swine influenza of any one of the preceding embodiments, wherein the modified live H1 virus of swine influenza contains HA and NA from A/swine/Minnesota/37866/1999 (H1N1) and PB2, PB1, PA, NP, M from A/Swine/Texas/4199-2/98 (H3N2) and the NS1-126 gene is from A/Swine/Texas/4199-2/98 (H3N2).

The modified live H1 virus of swine influenza of any one of the preceding embodiments, wherein the modified live H1 virus of swine influenza is a chimeric of A/swine/Minnesota/37866/1999 and TX/98/del 126.

The modified live H1 virus of swine influenza of any one of the preceding embodiments, wherein the modified live H1 virus of swine influenza a) comprises a nucleic acid sequence of gene segments having the NA and HA genes whose cDNA has greater than 70% identity to the nucleic acid sequence as set forth in SEQ ID NO:5 or SEQ ID NO:6, or b) comprises a nucleic sequence of gene segments having the NA and HA genes encoding NA and HA proteins having an amino acid sequence with greater than 70% identity to the amino acid sequence as set forth in SEQ ID NO:7 or SEQ ID NO:8, or c) comprises a NA and HA protein having an amino acid sequence with greater than 70% identity to the amino acid sequence as set forth in SEQ ID NO:7 or SEQ ID NO:8.

The modified live H1 virus of swine influenza of any one of the preceding embodiments, wherein the modified live H1 virus of swine influenza a) comprises a nucleic acid sequences of gene segments having the NA and HA genes whose cDNA has at least 70%, at least 75%, at least 80%, at least 85%, at least 90%, at least 91%, at least 92%, at least 93%, at least 94%, at least 95%, at least 96%, at least 97%, at least 98% or at least 99% identity to the nucleic acid sequence as set forth in SEQ ID NO:5 or SEQ ID NO:6, or b) comprises a nucleic sequences of gene segments having the NA and HA genes encoding NA and HA proteins having amino acid sequences with at least 70%, at least 75%, at least 80%, at least 85%, at least 90%, least 91%, at least 92%, at least 93%, at least 94%, at least 95%, at least 96%, at least 97%, at least 98% or at least 99% identity to the amino acid sequence as set forth in SEQ ID NO:7 or SEQ ID NO:8, or c) comprises a NA and HA protein having an amino acid sequence with at least 70%, at least 75%, at least 80%, at least 85%, at least 90%, at least 91%, at least 92%, at least 93%, at least 94%, at least 95%, at least 96%, at least 97%, at least 98% or at least 99% identity the amino acid sequence as set forth in SEQ ID NO:7 or SEQ ID NO:8.

An immunogenic composition comprising the modified live H1 virus of swine influenza of any one of the preceding embodiments.

The immunogenic composition of the above embodiment, wherein the immunogenic composition is formulated for a single-dose administration.

The immunogenic composition comprising the modified live H1 virus of swine influenza of any one of the preceding embodiments, wherein the immunogenic composition is administered intranasal.

The immunogenic composition comprising the modified live H1 virus of swine influenza of any one of the preceding embodiments, wherein the immunogenic composition is safe for sows during pregnancy and lactation.

The immunogenic composition comprising the modified live H1 virus of swine influenza of any one of the preceding embodiments, wherein the immunogenic composition is safe for pigs within the first two weeks of age, preferably within the first week of age.

The immunogenic composition comprising the modified live H1 virus of swine influenza of any one of the preceding embodiments, wherein the immunogenic composition is safe for pigs within the first day of age.

The immunogenic composition comprising the modified live H1 virus of swine influenza of any one of the preceding embodiments, wherein the immunogenic composition further comprises a pharmaceutically acceptable carrier.

The immunogenic composition comprising the modified live H1 virus of swine influenza of any one of the preceding embodiments, wherein the immunogenic composition comprises 2 to 8 $\log_{10}$ of the modified live H1 virus of swine influenza.

The immunogenic composition comprising the modified live H1 virus of swine influenza of any one of the preceding embodiments, wherein the immunogenic composition comprises 2 to 6 $\log_{10}$ of the modified live H1 virus of swine influenza.

The immunogenic composition comprising the modified live H1 virus of swine influenza of any one of the preceding embodiments, wherein the immunogenic composition comprises 2 to 4 $\log_{10}$ of the modified live H1 virus of swine influenza.

The immunogenic composition comprising the modified live H1 virus of swine influenza of any one of the preceding embodiments, wherein the immunogenic composition is a vaccine.

The immunogenic composition comprising the modified live H1 virus of swine influenza of any one of the preceding embodiments, wherein the immunogenic composition is effective in the treatment and/or prophylaxis of clinical signs caused by SIV in a subject of need.

A method for immunizing a subject comprising administering to such subject an immunogenic composition comprising the modified live H1 virus of swine influenza of any one of the preceding embodiments.

A method of treating or preventing clinical signs caused by swine influenza virus in a subject of need, the method comprising administering to the subject a therapeutically effective amount of an immunogenic composition comprising the modified live H1 virus of swine influenza of any one of the preceding embodiments.

A method of reducing the viral shedding in a subject of need, in comparison to a subject of a non-immunized control group of the same species, the method comprising administering to the subject a therapeutically effective amount of an immunogenic composition comprising the modified live H1 virus of swine influenza of any one of the preceding embodiments.

A method of vaccinating a subject having anti-SIV antibodies comprising the step of administering to said animal a single effective dose of an immunogenic composition comprising the modified live H1 virus of swine influenza of any one of the preceding embodiments.

A method for preventing or reducing early SIV infections in a subject, the method comprising administering to the subject a therapeutically effective amount of an immunogenic composition comprising the modified live H1 virus of swine influenza of any one of the preceding embodiments.

The method of any one of the preceding embodiments comprising the modified live H1 virus of swine influenza of any one of the preceding embodiments, wherein said subject is selected from the list consisting of swine, cattle, cat and dog.

The method of any one of the preceding embodiments comprising the modified live H1 virus of swine influenza of any one of the preceding embodiments, wherein the immunogenic composition is administered once.

The method of any one of the preceding embodiments comprising the modified live H1 virus of swine influenza of any one of the preceding embodiments, wherein the immunogenic composition is administered at two or more doses.

The method of any one of the preceding embodiments comprising the modified live H1 virus of swine influenza of any one of the preceding embodiments, wherein the immunogenic composition is administered intranasal.

The method of any one of the preceding embodiments comprising the modified live H1 virus of swine influenza of any one of the preceding embodiments, wherein the subject is Swine influenza virus maternal antibody negative.

The method of any one of the preceding embodiments comprising the modified live H1 virus of swine influenza of any one of the preceding embodiments, wherein the immunogenic composition is administered to sows during pregnancy and lactation.

The method of any one of the preceding embodiments comprising the modified live H1 virus of swine influenza of any one of the preceding embodiments, wherein the immunogenic composition is administered to pigs within the first month of age.

The method of any one of the preceding embodiments comprising the modified live H1 virus of swine influenza of any one of the preceding embodiments, wherein the immunogenic composition is administered to pigs within the first two weeks of age, preferably within the first week of age.

The method of any one of the preceding embodiments comprising the modified live H1 virus of swine influenza of any one of the preceding embodiments, wherein the immunogenic composition is administered to pigs at day 1 or 2 of age.

The method of any one of the preceding embodiments comprising the modified live H1 virus of swine influenza of any one of the preceding embodiments, wherein the immunogenic composition is administered to pigs within the first day of age.

The method of any one of the preceding embodiments comprising the modified live H1 virus of swine influenza of any one of the preceding embodiments, wherein the subject is Swine influenza virus maternal antibody positive.

The method of any one of the preceding embodiments comprising the modified live H1 virus of swine influenza of any one of the preceding embodiments, wherein the immunogenic composition comprises 2 to 8 $\log_{10}$ of the modified live H1 virus of swine influenza.

The method of any one of the preceding embodiments comprising the modified live H1 virus of swine influenza of any one of the preceding embodiments, wherein the immunogenic composition comprises 2 to 6 $\log_{10}$ of the modified live H1 virus of swine influenza.

The method of any one of the preceding embodiments comprising the modified live H1 virus of swine influenza of any one of the preceding embodiments, wherein the immunogenic composition comprises 2 to 4 $\log_{10}$ of the modified live H1 virus of swine influenza.

The method of any one of the preceding embodiments comprising the modified live H1 virus of swine influenza of any one of the preceding embodiments, wherein said method results in an improvement in an efficacy parameter selected from the group consisting of: a reduction in the weight loss, a lower virus load, a reduction in lung lesions, a reduced shedding, a reduced rectal temperature, or combinations thereof, in comparison to a subject of a non-immunized control group of the same species.

The method of any one of the preceding embodiments comprising the modified live H1 virus of swine influenza of any one of the preceding embodiments, wherein the treatment or prophylaxis results in shortening of the virus load phase as compared to animals of a non-treated control group of the same species.

The method of any one of the preceding embodiments comprising the modified live H1 virus of swine influenza of any one of the preceding embodiments, wherein the treatment or prophylaxis results in a reduction of the shedding from day 5 after challenge or infection.

The method of any one of the preceding embodiments comprising the modified live H1 virus of swine influenza of any one of the preceding embodiments, wherein the treatment or prophylaxis results in a reduction of the shedding from day 1 or 2 after challenge or infection.

A method of immunizing a subject, comprising administering to a subject an immunogenic composition comprising a H3N2 NS1 deletion mutant of swine influenza virus within the first two weeks of age.

A method of treating or preventing clinical signs caused by swine influenza virus in a subject of need, the method comprising administering to the subject a therapeutically effective amount of an immunogenic composition comprising a H3N2 NS1 deletion mutant of swine influenza virus within the first two weeks of age.

A method of reducing the viral shedding in a subject of need, in comparison to a subject of a non-immunized control group of the same species, the method comprising administering to the subject a therapeutically effective amount of an immunogenic composition comprising a H3N2 NS1 deletion mutant of swine influenza virus within the first two weeks of age.

A method of vaccinating a subject having anti-SIV antibodies comprising the step of administering to said animal a single effective dose of an immunogenic composition comprising a H3N2 NS1 deletion mutant of swine influenza virus within the first two weeks of age.

A method for preventing or reducing early SIV infections in a subject, the method comprising administering to the subject a therapeutically effective amount of an immunogenic composition comprising a H3N2 NS1 deletion mutant of swine influenza virus within the first two weeks of age.

The method of any one of the preceding embodiments comprising administering to a subject an immunogenic composition comprising a H3N2 NS1 deletion mutant of swine influenza virus, wherein the H3N2 NS1 deletion mutant of swine influenza virus encodes for a carboxy-terminal truncated NS1 protein comprising NS1 amino acids 1 through 124, 1 through 125, 1 through 126, 1 through 127 or 1 through 128, wherein the amino terminal amino acid is number 1.

The method of any one of the preceding embodiments comprising administering to a subject an immunogenic composition comprising a H3N2 NS1 deletion mutant of swine influenza virus, wherein the H3N2 NS1 deletion mutant of swine influenza virus encodes for a carboxy-terminal truncated NS1 protein comprising NS1 amino acids 1 through 126, wherein the amino terminal amino acid is number 1.

The method of any one of the preceding embodiments comprising administering to a subject an immunogenic composition comprising a H3N2 NS1 deletion mutant of swine influenza virus, wherein the H3N2 NS1 deletion mutant of swine influenza virus encodes for a carboxy-terminal truncated NS1 protein resulting in a deletion of 91, 92, 93 or 94 amino acid residues from the carboxy terminus of NS1.

The method of any one of the preceding embodiments comprising administering to a subject an immunogenic composition comprising a H3N2 NS1 deletion mutant of swine influenza virus, wherein the NS1 gene or protein of the H3N2 NS1 deletion mutant swine influenza virus is from A/Swine/Texas/4199-2/98.

The method of any one of the preceding embodiments comprising administering to a subject an immunogenic composition comprising a H3N2 NS1 deletion mutant of swine influenza virus, wherein the H3N2 NS1 deletion mutant of swine influenza virus is TX/98/del 126.

The method of any one of the preceding embodiments comprising administering to a subject an immunogenic composition comprising a H3N2 NS1 deletion mutant of swine influenza virus, wherein the H3N2 NS1 deletion mutant of swine influenza virus contains the HA, NA, PB2, PB1, PA, NP, and M from A/Swine/Texas/4199-2/98 and the NS1-126 gene is from A/Swine/Texas/4199-2/98.

The method of any one of the preceding embodiments comprising administering to a subject an immunogenic composition comprising a H3N2 NS1 deletion mutant of swine influenza virus, wherein the H3N2 NS1 deletion mutant of swine influenza virus is the H3N2 NS1 deletion mutant of swine influenza virus described in WO 2006/083286 A2 designated as TX/98/del1126.

The method of any one the preceding of embodiments comprising administering to a subject an immunogenic composition comprising a H3N2 NS1 deletion mutant of swine influenza virus, wherein the H3N2 NS1 deletion mutant of swine influenza virus comprises a nucleic acid sequence of gene segments having the NA and HA genes whose cDNA has at least 70% identity to the nucleic acid sequence as set forth in SEQ ID NO:1 or SEQ ID NO:2, or comprises a nucleic acid sequence of gene segments having the NA and HA genes encoding NA and HA proteins having an amino acid sequence with at least 70% identity to the amino acid sequence as set forth in SEQ ID NO:3 or SEQ ID NO:4, or comprises a NA and HA protein having an amino acid sequence with at least 70% identity to the amino acid sequence as set forth in SEQ ID NO:3 or SEQ ID NO:4.

The method of any one of the preceding embodiments comprising administering to a subject an immunogenic composition comprising a H3N2 NS1 deletion mutant of swine influenza virus, wherein the H3N2 NS1 deletion mutant of swine influenza virus comprises a nucleic acid sequences of gene segments having the NA and HA genes whose cDNA has at least 70%, at least 75%, at least 80%, at least 85%, at least 90%, at least 91%, at least 92%, at least 93%, at least 94%, at least 95%, at least 96%, at least 97%, at least 98% or at least 99% identity to the nucleic acid sequence as set forth in SEQ ID NO:1 or SEQ ID NO:2, or comprises a nucleic sequences of gene segments having the NA and HA genes encoding NA and HA proteins having amino acid sequences with at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:3 or SEQ ID NO:4, or comprises a NA and HA protein having an amino acid sequence with at least 70%, at least 75%, at least 80%, at least 85%, at least 90%, at least 91%, at least 92%, at least 93%, at least 94%, at least 95%, at least 96%, at least 97%, at least 98% or at least 99% identity to the amino acid sequence as set forth in SEQ ID NO:3 or SEQ ID NO:4.

The method of any one of the preceding embodiments comprising administering to a subject an immunogenic composition comprising a H3N2 NS1 deletion mutant of swine influenza virus, wherein the subject is selected from the list consisting of swine, cattle, cat and dog.

The method of any one of the preceding embodiments comprising administering to a subject an immunogenic composition comprising a H3N2 NS1 deletion mutant of swine influenza virus, wherein the immunogenic composition is administered once.

The method of any one of the preceding embodiments comprising administering to a subject an immunogenic composition comprising a H3N2 NS1 deletion mutant of swine influenza virus, wherein the immunogenic composition is administered at two or more doses.

The method of any one of the preceding embodiments comprising administering to a subject an immunogenic composition comprising a H3N2 NS1 deletion mutant of swine influenza virus, wherein the immunogenic composition is administered intranasal.

The method of any one of the preceding embodiments comprising administering to a subject an immunogenic composition comprising a H3N2 NS1 deletion mutant of swine influenza virus, wherein the subject is Swine influenza virus maternal antibody negative.

The method of any one of the preceding embodiments comprising administering to a subject an immunogenic composition comprising a H3N2 NS1 deletion mutant of swine influenza virus, wherein the immunogenic composition is administered to sows during pregnancy and lactation.

The method of any one of the preceding embodiments comprising administering to a subject an immunogenic composition comprising a H3N2 NS1 deletion mutant of swine influenza virus, wherein the immunogenic composition is administered to pigs within the first week of age.

The method of any one of the preceding embodiments comprising administering to a subject an immunogenic composition comprising a H3N2 NS1 deletion mutant of swine influenza virus, wherein the immunogenic composition is administered to pigs at day 1 or day 2 of age.

The method of any one of the preceding embodiments comprising administering to a subject an immunogenic composition comprising a H3N2 NS1 deletion mutant of swine influenza virus, wherein the immunogenic composition is administered to pigs within the first day of age.

The method of any one of the preceding embodiments comprising administering to a subject an immunogenic composition comprising a H3N2 NS1 deletion mutant of swine influenza virus, wherein the subject is Swine influenza virus maternal antibody positive.

The method of any one of the preceding embodiments comprising administering to a subject an immunogenic composition comprising a H3N2 NS1 deletion mutant of swine influenza virus, wherein the immunogenic composition comprises 2 to 8 $\log_{10}$ of the H3N2 NS1 deletion mutant of swine influenza virus.

The method of any one of the preceding embodiments comprising administering to a subject an immunogenic composition comprising a H3N2 NS1 deletion mutant of swine influenza virus, wherein the immunogenic composition comprises 2 to 6 $\log_{10}$ of the H3N2 NS1 deletion mutant of swine influenza virus.

The method of any one of the preceding embodiments comprising administering to a subject an immunogenic composition comprising a H3N2 NS1 deletion mutant of swine influenza virus, wherein the immunogenic composition comprises 2 to 4 $\log_{in}$ of the H3N2 NS1 deletion mutant of swine influenza virus.

The method of any one of the preceding embodiments comprising administering to a subject an immunogenic composition comprising a H3N2 NS1 deletion mutant of swine influenza virus, wherein said method results in an improvement in an efficacy parameter selected from the group consisting of: a reduction in weight loss, a lower virus load, a reduction in lung lesions, a reduced shedding, a reduced rectal temperature, or combinations thereof, in comparison to a subject of a non-immunized control group of the same species.

The method of any one of the preceding embodiments comprising administering to a subject an immunogenic composition comprising a H3N2 NS1 deletion mutant of swine influenza virus, wherein the treatment or prophylaxis results in a reduction of the shedding from day 5 after challenge or infection.

The method of any one of the preceding embodiments comprising administering to a subject an immunogenic composition comprising a H3N2 NS1 deletion mutant of swine influenza virus, wherein the treatment or prophylaxis results in a reduction of the shedding from day 1 after challenge or infection.

The method of any one of the preceding embodiments comprising administering to a subject an immunogenic composition comprising a H3N2 NS1 deletion mutant of swine influenza virus, wherein the method provides protection against a heterologous challenge.

The method of any one of the preceding embodiments comprising administering to a subject an immunogenic composition comprising a H3N2 NS1 deletion mutant of swine influenza virus wherein the method provides protection against a H1 challenge.

The method of any one of the preceding embodiments comprising administering to a subject an immunogenic composition comprising a H3N2 NS1 deletion mutant of swine influenza virus, wherein the method provides protection against a H1N1 challenge.

EXAMPLES

The following examples are only intended to illustrate the present invention. They shall not limit the scope of the claims in any way.

Example 1

Methods Used in Propagation of the Modified Live Vaccine Isolates and for Formulation of the Bivalent Vaccine The propagation of the modified live vaccine isolates can be accomplished using different systems. In this example the materials and methods are described for two different systems that have been evaluated to generate the antigen and ultimately the bivalent vaccine.

Genetic Characteristics of the Modified Live Vaccine Isolates in the Bivalent Vaccine Using reverse genetics a H1N1 NS1 mutant and a H3N2 NS1 mutant each encoding a carboxy-truncated NS1 protein have been generated. The H3N2 NS1 mutant already has been described in Solorzano et al. 2005 (J Virol 79:7535-7543), Vincent et al 2012 (Journal of Virology 19: 10597 to 10605) and WO 2006/083286 A2.

For H1N1, the hemagglutinin (HA) and neuraminidase (NA) genes from the parent H1N1 (A/swine/Minnesota/37866/1999) were combined with the PB2, PB1, PA, NP, M and NS-126 genes from (A/Swine/Texas/4199-2/98). The generated H1N1 NS1 mutant therefore contained 2 genes from the H1N1 parent and 6 genes from the H3N2 parent.

For H3N2, the HA, NA, PB2, PB1, PA, NP, M and NS-126 genes from A/Swine/Texas/4199-2/98 (H3N2) were combined and the resulting virus was designated TX98 H3N2 NS1 SIV.

Growth of the Modified Live Vaccine Isolates in Embryonated Chicken Eggs and Formulation of the Bivalent Vaccine Six to seven day embryonated chicken eggs are inoculated by injection of one or the other modified live viruses into the allantoic fluid (allantoic inoculation). Separate pre-labeled sets of eggs are used for growing the H1N1 NS1 isolate and the H3N2 NS1 isolate. After inoculation with the respective virus the eggs are incubated for three to four days then chilled for at least four hours before the virus containing allantoic fluid is harvested. Aliquots are made of the harvested allantoic fluid which contains high concentrations of the respective modified live virus. All of the viruses containing aliquots are stored at or below −40° C. until they are needed for vaccine formulation.

Prior to vaccine formulation an aliquot of each virus congaing allantoic fluid is thawed and titrations are performed to determine the concentration of virus so that plans for vaccine formulations can be made. Once the quantity of virus is determined for the viral stocks the two isolates can be blended together along with phosphate buffered saline directly prior to vaccination to reach the desired inclusion for use in an animal study.

Growth of the Modified Live Vaccine Isolates in Cell Based Tissue Culture and Formulation of the Bivalent Vaccine A vessel containing a six to eight day old EVERO cell culture is inoculated by addition of one or the other modified live virus into the vessel after a media change and the addition of trypsin containing media. Separate pre-labeled sets of vessels are used for growing the H1N1 isolate and the H3N2 isolate. After inoculation with their respective virus the vessels are incubated for up to seven days then harvested. Aliquots are made of the harvested media that contains high concentrations of the respective modified live virus. All of the virus aliquots are stored at or below −40° C. until they were needed for vaccine formulation.

Prior to vaccine formulation an aliquot of each virus congaing media is thawed and titrations are performed to determine the concentration of virus so that plans for vaccine formulations can be made. Once the quantity of virus is determined for the viral stocks the two isolates can be blended together along with a stabilizer (sucrose gelatin stabilizer) and phosphate buffered saline (only if needed) directly prior to being lyophilized. The volume of each of the virus stocks is controlled in order to reach the desired inclusion level for use in future animal studies. Once blended the bivalent vaccine material is aseptically transferred to sterile glass bottles then the bottles are loaded into a lyophilizer. The lyophilizer is then run through a freeze dry cycle to prepare the vaccine for storage at about 4° C. until use in an animal study.

Directly prior to vaccination the lyophilized bivalent vaccine contained within the glass bottle is rehydrated with an appropriate volume of phosphate buffered saline in order to achieve the desired titer for use in the animal study.

Example #2

Single Dose Intranasal Administration at Various Doses to Pigs 1-6 Days Old Negative for Maternal Immunity Resulting in Reduced Nasal Shedding, Reduced Isolation From Lungs, and Reduced Lung Lesions Study design considerations, vaccine formulation, dosing information, and efficacy summaries.

Study 1

On study day 0 the piglets (housed in separate rooms by group) were vaccinated with egg propagated vaccine virus at the inclusion levels indicated in Table 1. Only healthy pigs of about one week of age or less were allowed to be enrolled into the study as determined by a health examination prior to vaccination. The pigs were each vaccinated with 2 mL of the respective vaccine by applying 1 mL to each nostril. Feed rations were appropriate for the age and condition of test animals according to facility standard operating procedures. Water was provided ad libitum to the test animals throughout the study.

TABLE 1

Study 1: Vaccine Inclusion Levels

| Group ID | H1N1 Titer ($\log_{10}TCID_{50}$/mL) | H3N2 Titer ($\log_{10}TCID_{50}$/mL) |
| --- | --- | --- |
| Higher Dose | 7.28 | 8.10 |
| Lower Dose | 6.28 | 7.10 |

Prior to challenge the piglets were weaned and moved into challenge rooms, then on or about study day 36 the piglets were challenged with 2 mL of the heterologous H1N2 (A/Swine/North Carolina/001169/2006) SIV isolate at a titer of 7.10 $\log_{10}$/mL by intratracheal inoculation under anesthesia. Nasal swabs were collected daily from challenge until necropsy and then the lungs were scored for lesions and lung tissue was collected at necropsy. The efficacy of the vaccine was evaluated by its ability to reduce the number of virus isolations in the nasal swabs and from the lung tissues as well as its ability to reduce the lung lesion in the vaccinated groups.

As shown in Table 2 the animals vaccinated at both the higher dose and the lower dose were protected from the heterologous challenge as evidenced by reductions in virus isolation from nasal swabs and from lung tissue, as well as a reduction in lung lesions when comparisons are made to the group of pigs that were challenged after having received no vaccination.

TABLE 2

Study 1: Vaccine Efficacy Summary

| | From Challenge Through End of Study | | |
| --- | --- | --- | --- |
| Group | % Nasal Swab Virus Positive | % Lung Tissue Virus Positive | Group Average Lung Score |
| Higher Dose | 32% | 0% | 9.5% |
| Lower Dose | 33% | 0% | 8.5% |
| No Vaccine | 100% | 47% | 28.2% |

The conclusion made from the data generated in this study was that there are reductions in the amount of virus shed from the nasal passages, there are reductions in the virus load in the lungs as well as reductions in the primary efficacy parameter of gross lung lesions, which all taken together indicates that a single intranasal dose at the two inclusion levels used in this study is efficacious in naïve pigs vaccinated within one to six days of age.

Study 2

On study day 0 the piglets (housed in separate rooms by group) were vaccinated with reconstituted lyophilized tissue culture (EVERO cell) propagated vaccine virus at the inclusion levels indicated in Table 3. Only healthy pigs of about one week of age or less were allowed to be enrolled into the study as determined by a health examination prior to vaccination. The pigs were each vaccinated with 1 mL of the respective vaccine by applying the full volume to one nostril. Feed rations were appropriate for the age and condition of test animals according to facility standard operating procedures. Water was provided ad libitum to the test animals throughout the study.

TABLE 3

Study 2: Vaccine Inclusion Levels

| Group ID | H1N1 Titer ($\log_{10}FAID_{50}$/mL) | H3N2 Titer ($\log_{10}FAID_{50}$/mL) |
| --- | --- | --- |
| Higher Dose | 5.7 | 6.6 |
| Medium Dose | 5.1 | 6.0 |
| Lower Dose | 3.7 | 4.8 |

Prior to challenge the piglets were weaned and moved into challenge rooms, then on or about study day 25 the piglets were challenged with 2 mL of the heterologous H1N2 (A/Swine/North Carolina/001169/2006) SIV isolate at a titer of 7.96 $\log_{10}$/mL by intratracheal inoculation under anesthesia. Nasal swabs were collected daily from challenge until necropsy and then the lungs were scored for lesions and lung lavage fluid was collected at necropsy. The efficacy of the vaccine was evaluated by its ability to reduce the number of virus isolations in the nasal swabs and from the lung lavage fluid as well as its ability to reduce the lung lesions in the vaccinated groups.

As shown in Table 4 the animals vaccinated at all of the doses were protected from the heterologous challenge as evidenced by reductions in virus isolation from nasal swabs and from lung lavage fluid, as well as a reduction in lung lesions when comparisons are made to the group of pigs that were challenged after having received no vaccination.

TABLE 4

Study 2: Vaccine Efficacy Summary

| | From Challenge Through End of Study | | |
| --- | --- | --- | --- |
| Group | % Nasal Swab Ever Virus Positive | % Lung Lavage Virus Positive | Group Average Lung Score |
| Higher Dose | 45% | 0% | 10.3% |
| Medium Dose | 50% | 0% | 5.3% |
| Lower Dose | 48% | 0% | 5.8% |
| No Vaccine | 100% | 10% | 18.3% |

The conclusion made from the data generated in this study was that there are reductions in the amount of virus shed from the nasal passages, there are reductions in the virus isolation positive lungs as well as reductions in the primary efficacy parameter of gross lung lesions, which all taken together indicates that a single intranasal dose at the three inclusion levels used in this study is efficacious in naïve pigs vaccinated within one to six days of age.

Study 3

On study day 0 the piglets (housed in separate rooms by group) were vaccinated with reconstituted lyophilized tissue culture (EVERO cell) propagated vaccine virus at the inclusion levels indicated in Table 5. Only healthy pigs of about one week of age or less were allowed to be enrolled into the study as determined by a health examination prior to vaccination. The pigs were each vaccinated with 1 mL of the respective vaccine by applying the full volume to one nostril. Feed rations were appropriate for the age and condition of test animals according to facility standard operating procedures. Water was provided ad libitum to the test animals throughout the study.

TABLE 5

Study 3 Vaccine Inclusion Levels

| Group ID | H1N1 Titer ($\log_{10}FAID_{50}$/mL) | H3N2 Titer ($\log_{10}FAID_{50}$/mL) |
|---|---|---|
| Higher Dose | 4.7 | 5.8 |
| Medium Dose | 3.6 | 4.7 |
| Lower Dose | 2.9 | 3.8 |

Prior to challenge the piglets were weaned and moved into challenge rooms, then on or about study day 30 the piglets were challenged with 2 mL of the heterologous H3N2 (A/Swine/Nebraska/97901-10/2008) SIV isolate at a titer of 6.09 $\log_{10}$/mL by intratracheal inoculation under anesthesia. Nasal swabs were collected daily from challenge until necropsy and then the lungs were scored for lesions and lung lavage fluid was collected at necropsy. The efficacy of the vaccine was evaluated by its ability to reduce the number of virus isolations in the nasal swabs and from the lung lavage fluid as well as its ability to reduce the lung lesions in the vaccinated groups.

As shown in Table 6 the animals vaccinated at all of the doses were protected from the heterologous challenge as evidenced by reductions in virus isolation from nasal swabs and from lung lavage fluid, as well as a reduction in lung lesions when comparisons are made to the group of pigs that were challenged after having received no vaccination.

TABLE 6

Study 3 Vaccine Efficacy Summary

| | From Challenge Through End of Study | | |
|---|---|---|---|
| Group | % Nasal Swab Ever Virus Positive | % Lung Lavage Virus Positive | Group Average Lung Score |
| Higher Dose | 46% | 0% | 2.5% |
| Medium Dose | 43% | 0% | 3.4% |
| Lower Dose | 50% | 8% | 4.5% |
| No Vaccine | 96% | 65% | 9.6% |

The conclusion made from the data generated in this study was that there are reductions in the amount of virus shed from the nasal passages, there are reductions in the virus isolation positive lungs as well as reductions in the primary efficacy parameter of gross lung lesions, which all taken together indicates that a single intranasal dose at the three inclusion levels used in this study is efficacious in naïve pigs vaccinated within one to six days of age.

Example #3

Single Dose Intranasal Administration to Pigs Three Weeks Old Negative for Maternal Immunity Study design considerations, vaccine formulation, dosing information, and efficacy summaries.

Study 4

On study day 0 the pigs (housed in separate rooms by challenge group) were vaccinated with egg propagated vaccine virus at the inclusion levels indicated in Table 7. Only healthy pigs of about three weeks of age were allowed to be enrolled into the study as determined by a health examination prior to vaccination. The pigs were each vaccinated with 4 mL of the vaccine by applying 2 mL to each nostril. Feed rations were appropriate for the age and condition of test animals according to facility standard operating procedures. Water was provided ad libitum to the test animals throughout the study.

TABLE 7

Study 4 Vaccine Inclusion Levels

| Group ID | H1N1 Titer ($\log_{10}TCID_{50}$/mL) | H3N2 Titer ($\log_{10}TCID_{50}$/mL) |
|---|---|---|
| Bivalent | 7.38 | 7.97 |

On or about study day 28 the piglets were challenged with either 2 mL of the heterologous H1N1 (A/Swine/Indiana/1726/88) SIV isolate at a titer of 6.63 $\log_{10}$/mL or 2 mL of the heterologous H3N2 (A/Swine/Nebraska/97901-10/2008) SIV isolate at a titer of 7.58 $\log_{10}$/mL by intratracheal inoculation under anesthesia. Nasal swabs were collected daily from challenge until necropsy and then the lungs were scored for lesions and lung tissue was collected at necropsy. The efficacy of the vaccine was evaluated by its ability to reduce the number of virus isolations in the nasal swabs and from the lung tissues as well as its ability to reduce the lung lesion in the vaccinated groups.

As shown in Table 8 the vaccinated animals were protected from the heterologous H1N1 challenge as evidenced by reductions in virus isolation from nasal swabs and from lung tissue, as well as a reduction in lung lesions when comparisons are made to the group of pigs that were challenged after having received no vaccination. Similar results (data not shown) were seen for pigs that were vacated intramuscularly with the same vaccine. Also shown in Table 8 the vaccinated animals were protected from the heterologous H3N2 challenge as evidenced by reductions in virus isolation from lung tissue, as well as a reduction in lung lesions when comparisons are made to the group of pigs that were challenged after having received no vaccination. Nasal swabs were collected from the day of challenge (before challenge) through the day of necropsy. Since none of the bivalent vaccinated animals shed virus after the H1N1 challenge and the non-vaccinated animals started shedding at two days post challenge (data not shown) the bivalent vaccine prevented shedding of challenge virus from the vaccinated pigs at two days post challenge.

TABLE 8

Study 4 Vaccine Efficacy Summary

| | | From Challenge Through End of Study | | |
|---|---|---|---|---|
| Group | Challenge Virus | % Nasal Swab Virus Positive | % Lung Tissue Virus Positive | Group Average Lung Score |
| Bivalent | H1N1 | 0% | 0% | 0.5% |
| No Vaccine | Indiana | 100% | 100% | 13.0% |
| Bivalent | H3N2 | 0% | 0% | 0.8% |
| No Vaccine | Nebraska | 0% | 10% | 5.2% |

The conclusion made from the data generated in this study was that there are reductions in the amount of virus shed from the nasal passages following an H1N1 challenge and there are reductions in the virus load in the lungs as well as reductions in the primary efficacy parameter of gross lung lesions after challenge with either of the viruses. A single intranasal dose given at the inclusion level used in this study is efficacious in naïve pigs vaccinated at three weeks of age.

Example #4

Safety of a Single Dose Intranasal Administration During Pregnancy

Study design considerations, vaccine formulation, dosing information, and safety summaries.

Study 5

On or about study day minus 28 the eight gilts were vaccinated with egg propagated vaccine virus at the inclusion levels indicated in Table 9. Only healthy pregnant gilts were allowed to be enrolled into the study as determined by a health examination prior to vaccination. The gilts were each vaccinated with 2 mL of the vaccine by applying 1 mL to each nostril. Feed rations were appropriate for the age and condition of test animals according to facility standard operating procedures. Water was provided ad libitum to the test animals throughout the study.

TABLE 9

Study 5 Vaccine Inclusion Levels

| Group ID | H1N1 Titer ($\log_{10}TCID_{50}$/mL) | H3N2 Titer ($\log_{10}TCID_{50}$/mL) |
| --- | --- | --- |
| Bivalent | 6.52 | 7.71 |

After vaccination the safety of the vaccine was evaluated by observing and recording clinical signs daily for each of the vaccinated gilts. There were no major clinical signs recorded for any of the gilts between the time that they were vaccinated and when they farrowed. There were however some minor clinical signs recorded for three of the gilts, but none of the signs were observed until the fifth day after vaccination and none of the signs persisted for more than four days.

The conclusion made from the data generated in this study is that the vaccine is safe when administered to gilts at the inclusion levels used in this study when vaccination is done around the ninetieth day of gestation.

Example 5

Single Dose Intranasal Administration to Pigs at 1-8 Days Old Positive for Maternal Immunity Study design considerations, vaccine formulation, dosing information, and efficacy summaries.

Study 5

On or about study day minus 28, eight gilts were vaccinated with egg propagated vaccine virus at the inclusion level indicated in Table 1 in order to induce maternal immunity. The gilts were each vaccinated with 2 mL of the vaccine by applying 1 mL to each nostril. All of the gilts farrowed prior to study day 0, at which time the piglets were vaccinated with egg propagated vaccine virus at the inclusion level indicated in Table 10. Only healthy pigs of about one week of age or less were allowed to be enrolled into the study as determined by a health examination prior to vaccination. The pigs were each vaccinated with 2 mL of the respective vaccine by applying 1 mL to each nostril. Feed rations were appropriate for the age and condition of test animals according to facility standard operating procedures. Water was provided ad libitum to the test animals throughout the study.

TABLE 10

Study 5 Vaccine Inclusion Levels

| Group ID | H1N1 Titer ($\log_{10}TCID_{50}$/mL) | H3N2 Titer ($\log_{10}TCID_{50}$/mL) |
| --- | --- | --- |
| Bivalent Gilts | 6.52 | 7.71 |
| Bivalent Pigs | 5.84 | 7.32 |

Prior to challenge the piglets were weaned and moved into a challenge room, then on or about study day 42 the piglets were challenged with 2 mL of the heterologous H1N2 (A/Swine/North Carolina/001169/2006) SIV isolate at a titer of 7.61 $\log_{10}$/mL by intratracheal inoculation under anesthesia. Nasal swabs were collected daily from challenge until necropsy and then the lungs were scored for lesions and lung lavage was collected at necropsy. The efficacy of the vaccine was evaluated by its ability to reduce the number of virus isolations in the nasal swabs and from the lung lavage as well as its ability to reduce the lung lesions in the vaccinated groups.

As shown in Table 11 the animals vaccinated with the bivalent vaccine were protected from the heterologous challenge as evidenced by reductions in virus isolation from nasal swabs and from lung lavage, as well as a reduction in lung lesions when comparisons are made to the group of pigs that were challenged after having received no vaccination.

TABLE 11

Study 5 Vaccine Efficacy Summary

| | From Challenge Through End of Study | | |
| --- | --- | --- | --- |
| Group | % Nasal Swab Virus Positive | % Lung Tissue Virus Positive | Group Average Lung Score |
| Bivalent | 38.3% | 0% | 1.9% |
| No Vaccine | 43.3% | 60% | 4.0% |

The conclusion made from the data generated in this study was that there are reductions in the amount of virus shed from the nasal passages, there are reductions in the virus load in the lungs as well as reductions in the primary efficacy parameter of gross lung lesions, which all taken together indicates that a single intranasal dose at the inclusion level used in this study is efficacious in maternal immunity positive pigs vaccinated within one to eight days of age.

Example 6

Advantageous Effect of Single Dose Intranasal Administration of Bivalent Vaccine Over Monovalent Vaccine Study design considerations, vaccine formulation, dosing information, and efficacy summaries.

Study 6 and Study 1

On study day 0 of the two respective studies the piglets (housed in separate rooms by group) were vaccinated with tissue culture (EVERO cell) propagated vaccine virus at the inclusion levels indicated in Table 12. Only healthy pigs of about one week of age or less were allowed to be enrolled into the studies as determined by a health examination prior to vaccination. In study 1 the pigs were each vaccinated with 1 mL of the monovalent vaccine by applying ½ mL to each nostril. In study 6 the pigs were each vaccinated with 1 mL of the bivalent vaccine by applying the full volume to the left nostril. Feed rations were appropriate for the age and condition of test animals according to facility standard operating procedures. Water was provided ad libitum to the test animals throughout the study.

TABLE 12

Study 1 and 6 Vaccine Inclusion Levels

| Study | Group ID | H1N1 Titer ($\log_{10}FAID_{50}/mL$) | H3N2 Titer ($\log_{10}FAID_{50}/mL$) |
|---|---|---|---|
| 1 | 2 Log | 2.17 | N/A |
|  | 3 Log | 2.98 | N/A |
|  | 4 Log | 3.65 | N/A |
|  | 5 Log | 4.99 | N/A |
| 6 | 3 Log | 2.81 | 2.84 |
|  | 4 Log | 3.99 | 4.00 |
|  | 5 Log | 4.56 | 4.63 |
|  | 6 Log | 5.48 | 5.66 |

N/A = not applicable

Prior to challenge in the two respective studies the piglets were weaned and moved into challenge rooms, then on or about study day 25 the piglets were challenged with 2 mL of the heterologous H1N2 (A/Swine/North Carolina/001169/2006) SIV isolate at a titer of 7.44 $\log_{10}$/mL in study 6 and 7.92 $\log_{10}$/mL in study 1 by intratracheal inoculation under anesthesia. Nasal swabs were collected daily from challenge until necropsy and then the lungs were scored for lesions and lung lavage fluid was collected at necropsy. The efficacy of the vaccine was evaluated by its ability to reduce the number of virus isolations in the nasal swabs and from the lung lavage fluid as well as its ability to reduce the lung lesions in the vaccinated groups.

As shown in Table 13 the animals vaccinated with the monovalent vaccine in study 6 required a dose of 4.99 $\log_{10}FAID_{50}/mL$ of the of the H1N1 vaccine virus before they were protected from the heterologous challenge. Protection is evidenced by a reduction in virus isolations from nasal swabs and from lung lavage fluid, as well as a reduction in lung lesions when comparisons are made to the group of pigs that were challenged after having received no vaccination in that same study.

Also shown in Table 2 the animals in study 1 required a dose of only 2.81 $\log_{10}FAID_{50}/mL$ of the H1N1 vaccine virus when it was administered in the bivalent vaccine with 2.84 $\log_{10}FAID_{50}/mL$ of the H3N2 vaccine virus before they were protected from the heterologous challenge. The calculated total dose of antigen included in the protective bivalent vaccine is 3.13 $\log_{10}FAID_{50}/mL$ when the quantities of each antigen are added together. Protection is evidenced by reductions in virus isolations from nasal swabs and from lung lavage fluid, as well as reductions in lung lesions when comparisons are made to the group of pigs that were challenged after having received no vaccination in that same study.

TABLE 13

Study 1 and 6 Vaccine Efficacy Summary

| | | From Challenge Through End of Study | | |
|---|---|---|---|---|
| Study | Group | % Nasal Swab Ever Virus Positive | % Lung Lavage Virus Positive | Group Average Lung Score |
| 1 | 5 Log | 27% | 0% | 8.0% |
|  | 4 Log | 13% | 0% | 11.2% |
|  | 3 Log | 93% | 13% | 13.1% |
|  | 2 Log | 90% | 40% | 10.1% |
|  | No Vaccine | 93% | 53% | 9.4% |
| 6 | 6 Log | 18% | 0% | 2.44% |
|  | 5 Log | 5% | 0% | 3.06% |
|  | 4 Log | 14% | 0% | 5.10% |
|  | 3 Log | 53% | 0% | 8.50% |
|  | No Vaccine | 100% | 14% | 11.37% |

The experimental data provided herein show that a combination of the H1N1 NS1 and H3N2 deletion mutant of swine influenza virus together is, surprisingly more potent than the aggregate effect of the individual components.

The synergistic effect of the bivalent vaccine of the present invention is very clearly demonstrated by its ability to provide protection when administered at a much lower inclusion level than what is required for the monovalent H1N1 vaccine. The bivalent vaccine of the present invention administered at a total dose of only 3.13 $\log_{10}FAID_{50}/mL$ provided protection as compared to the monovalent vaccine which showed a similar level of protection after being administered at a dose of 4.99 $\log_{10}FAID_{50}/mL$ (about 72-times more than the total dose of bivalent vaccine). Further, Vincent et al 2012 (Journal of Virology 19: 10597 to 10605) have shown that $1\times10^6$ $TCID_{50}$ (correspond to 6 $\log_{10}$ $FAID_{50}$) of the monovalent H3N2 provided protection (about 741-times more than the total dose of bivalent vaccine). Thus, the concentration of the H1 and H3 components in the bivalent vaccine are dramatically reduced compared to the concentrations needed in the monovalent vaccines. This is an unexpected surprising synergistic effect.

There is even further supporting evidence of the synergistic effect of the bivalent vaccine when the amount of challenge virus is considered. The monovalent vaccine even administered at the higher dose provided only a similar level of protection from a challenge of approximately 3-times less of the same challenge isolate.

The conclusion made from the data generated in these studies is that there are reductions in the amount of virus shed from the nasal passages, there are reductions in the virus isolation positive lungs as well as reductions in the primary efficacy parameter of gross lung lesions, at much lower doses of antigen when the vaccine is administered as a bivalent product as compared to when it is administered as a monovalent product. All taken together the data indicates that a single intranasal dose of the bivalent vaccine is more efficacious than the higher dose monovalent vaccine used in naïve pigs in these studies.

The synergistic combination of the present invention is advantageous since the chances of adverse effects are reduced. Additionally, a bivalent vaccine containing a lower concentration than the individual components will clearly be easier and cheaper to manufacture as well.

Moreover, there is a further advantageous surprising synergistic effect besides the above described synergistic concentration effect. The H3N2 component synergistically acts with the H1N1 component. The synergistic effect of the bivalent vaccine is very clearly demonstrated by its ability to provide protection from the heterologous H1N2 (A/Swine/North Carolina/001169/2006) SIV isolate. Thus, there is a cross protection effect. This effect is, further, synergistic because the bivalent vaccine of the present invention is administered at a much lower inclusion level than what is required for the monovalent vaccines as described above.

The sequences accompanying this application are hereby incorporated by reference in its entirety:

```
Nucleotide Sequence of NA of H3N2 (A/Swine/Texas/4199-2/98):
                                                                  SEQ ID NO: 1
       1    TATTGGTCTC AGGGAGCAAA AGCAGGAGTA AAGATGAATC CAAATCAAAA GATAATAACG
      61    ATTGGCTCTG TTTCTCTCAC TATTGCCACA ATGTGCTTCC TTATGCAAAT TGCCATCCTG
     121    GTAACTACTG TAACATTGCA TTTCAAGCAA TATGAATGCA ACTACCCCCC AAACAACCAA
     181    GTAATACTGT GTGAACCAAC AATAATAGAA AGAAACATAA CAGAGATAGT GTATCTGACC
     241    AACACCACCA TAGAGAAGGA ATATGCCCC AAACTAGCAG AATACAGAAA TTGGTCAAAG
     301    CCGCAATGTA AAATTACAGG ATTTGCACCT TTTTCCAAGG ACAATTCGAT TAGGCTTTCC
     361    GCTGGTGGGG ACATTTGGGT GACAAGAGAA CCTTATGTGT CATGCGATCC TGACAAGTGT
     421    TATCAATTTG CCCTTGGACA GGGAACAACA CTAAACAACA GGCATTCAAA TGACACAGTA
     481    CATGATAGGA CCCCTTATCG AACCCTATTG ATGAATGAGT TGGGTGTTCC ATTTCATTTG
     541    GGAACCAAGC AAGTGTGCAT AGCATGGTCC AGCTCAAGTT GTCACGATGG AAAAGCATGG
     601    CTGCATGTTT GTGTAACTGG GCATGATGAA AATGCAACTG CTAGCTTCAT TTACGATGGG
     661    AGGCTTGTAG ATAGTATTGG TTCATGGTCC AAAAAAATCC TCAGGACCCA GGAGTCGGAA
     721    TGCGTTTGTA TCAATGGAAC TTGTACAGTA GTAATGACTG ATGGGAGTGC TTCAGGAAGA
     781    GCTGATACTA AAATATTATT CATTGAGGAG GGGAAAATCG TTCATATTAG CCCATTGTTA
     841    GGAAGTGCTC AGCATGTCGA GGAGTGCTCC TGTTATCCTC GATATCCTGG TGTCAGATGT
     901    GTCTGCAGAG ACAACTGGAA AGGCTCCAAT AGGCCCATCG TAGATATAAA TGTAAAGGAT
     961    TATAGCATTG TTTCCAGTTA TGTGTGCTCA GGACTTGTTG GAGACACACC CAGAAAAAAC
    1021    GACAGATCCA GCAGTAGCAA TTGCCTGAAT CCTAACAATG AGGAAGGGGG TCATGGAGTG
    1081    AAAGGCTGGG CCTTTGATGA TGGAAATGAC GTGTGGATGG GAAGAACGAT CAACGAGAAG
    1141    TTACGCTCAG GTTATGAAAC CTTCAAAGTC ATTGAAGGCT GGTCCAAACC TAACTCCAAA
    1201    TTGCAGATAA ATAGGCAAGT CATAGTTGAC AGAGGTGATA GGTCCGGTTA TTCTGGCATT
    1261    TTCTCTGTTG AAGGCAAAAG CTGCATCAAT CGGTGCTTTT ATGTGGAGTT GATAAGGGGA
    1321    AGGAAACAGG AAACTGAAGT ATGGTGGACC TCAAACAGTA TTGTTGTGTT TTGTGGCACC
    1381    TCAGGTACAT ATGGAACAGG CTCATGGCCT GATGGGCGG ACATCAATCT CATGCCTATA
    1441    TAAGCTTTCG CAATTTTAGA AAAAACTCC TTGTTTCTAC TAATACGAGA CCATAT
Nucleotide Sequence of HA of H3N2 (A/Swine/Texas/4199-2/98):
                                                                  SEQ ID NO: 2
       1    TATTCGTCTC AGGGAGCAAA AGCAGGGGAT AATTCTATTA ACCATGAAGA CTATCATTGC
      61    TTTGAGCTAC ATTTTATGTC TGGTTTTCGC TCAAAAACTT CCCGGAAATG ACAACAGCAC
     121    AGCAACGCTG TGCCTGGGAC ACCATGCAGT GCCAAACGGA ACCCTAGTGA AAACAATCAC
     181    GAATGATCAA ATTGAAGTGA CTAATGCTAC TGAGCTGGTT CAGAGTTCCT CAACAGGTAG
     241    AATATGCGAC AGTCCTCACC GAATCCTTGA TGGAAAAAAC TGCACATTGA TAGATGCTCT
     301    ACTGGGAGAC CCTCATTGCG ATGGCTTTCA AAATAAGGAA TGGGACCTTT TTATTGAACG
     361    CAGCAAAGCT TACAGCAACT GTTACCCTTA TGATGTGCCG GATTATTCCT CCCTTAGGTC
     421    ACTAGTTGCC TCATCAGGCA CCCTGGAGTT TACCAATGAA GACTTCAATT GGACTGGGGT
     481    CGCTCAGGAT GGGGGAAGCT ATTCTTGCAA AAGGGGATCT GTTAAAAGTT TCTTTAGTAG
     541    ATTGAATTGG TTACACAAAT TAGAATACAA ATATCCAGCA CTGAACGTGA CTATGCCAAA
     601    CAATGACAAA TTTGACAAAT TGTACATTTG GGGGGTTCAC CACCCGAGCA CGGACAGTGA
```

-continued

```
 661   ACAAACCAGC CTGTATGTTC AAGCAATAGG GAGAGTCACA GTCTCTACCA AAAGTAGCCA
 721   ACAAACTGTA ATCCCGAACA TCGGGTCCAG ACCCTGGGTG AGGGGCATCT CCAGTAGAAT
 781   AAGCATCTAT TGGACAATAG TAAAACCGGG AGACATACTT TTGATTAGCA GCACAGGGAA
 841   TCTAATTGCT CCTCGGGGTT ACTTCAAAAT ACGAAATGGG AAAGCTCAA TAATGAGGTC
 901   AGATGCACCC ATTGACAACT GCTATTCTGA ATGCATCACT CCAAATGGAA GCATTCCCAA
 961   TGACAAACCT TTTCAAAATG TAAATAGGAT CACATATGGG GCCTGTCCCA AATATGTTAA
1021   GCAAAAAACC CTGAAATTGG CAACAGGGAT GCGGAATGTA CCAGAGAAAC AAACTAGAGG
1081   CATATTCGGC GCAATCGCAG GTTTCATAGA AAATGGTTGG GAGGGAATGG TAGACGGTTG
1141   GTACGGTTTC AGGCATCAAA ATTCTGAGGG CACAGGACAA GCAGCAGATC TTAAAAGCAC
1201   CCAAGCAGCA ATCGATCAAG TCAACGGGAA ATTGAATAGG TTAATCGAGA AACGAACGA
1261   GAAATTCCAT CAAATCGAAA AGAATTTTC AGAAGTAGAA GGGAGAATTC AGGACCTCGA
1321   GAAATATGTT GAAGACACTA AAATAGATC CTGGTCTTAC AACGCGGAGC TCCTTGTTGC
1381   CCTGGAGAAT CAACATACAA TTGATCTAAC TGACTCAGAA ATGAACAAAC TGTTTGAAAA
1441   AACAAGGAAG CAACTGAGGG AAAATGCTGA GGACATGGGC AATGGTTGCT TCAAAATATA
1501   CCACAAATGT GACAATGCCT GCATAGGGTC AATCAGAAAT GGAACTTATG ACCATGATGT
1561   ATACAGAGAC GAAGCATTAA ACAACCGGTT CCAGATCAAA GGTGTTGAGC TGAAATCAGG
1621   ATACAAAGAT TGGATCCTAT GGATTTCCTT TGCCATATCA TGCTTTTTGC TTTGTGTTGT
1681   TTTGCTGGGG TTCATCATGT GGGCCTGCCA AAAAGGCAAC ATTAGGTGCA ACATTTGCAT
1741   TTGAGTGCAT TAATTAAAAA CACCCTTGTT TCTACTAATA CGAGACGATA T
```

Amino Acid Sequence of NA of H3N2 (A/Swine/Texas/4199-2/98):
SEQ ID NO: 3

MNPNQKIITIGSVSLTIATMCFLMQTAILVTTVTLHFKQYECNYPPNNQVILCEPTIIERNI

TEIVYLTNTTIEKEICPKLAEYRNWSKPQCKITGFAPFSKDNSIRLSAGGDIWVTREPYVSC

DPDKCYQFALGQGTTLNNRHSNDTVHDRTPYRTLLMNELGVPFHLGTKQVCTAWSSSSCHDG

KAWLHVCVTGHDENATASFIYDGRLVDSIGSWSKKILRTQESECVCINGTCTVVMTDGSASG

RADTKILFIEEGKIVHISPLLGSAQHVEECSCYPRYPGVRCVCRDNWKGSNRPIVDINVKDY

SIVSSYVCSGLVGDTPRKNDRSSSSNCLNPNNEEGGHGVKGWAFDDGNDVWMGRTINEKLRS

GYETFKVIEGWSKPNSKLQINRQVIVDRGDRSGYSGIFSVEGKSCINRCFYVELIRGRKQET

EVWWTSNSIVVFCGTSGTYGTGSWPDGADINLMPI

Amino Acid Sequence of HA of H3N2 (A/Swine/Texas/4199-2/98):

SEQ ID NO: 4

MKTIIALSYILCLVFAQKLPGNDNSTATLCLGHHAVPNGTLVKTITNDQIEVTNATELVQSS

STGRICDSPHRILDGKNCTLIDALLGDPHCDGFQNKEWDLFIERSKAYSNCYPYDVPDYSSL

RSLVASSGTLEFTNEDFNWTGVAQDGGSYSCKRGSVKSFFSRLNWLHKLEYKYPALNVTMPN

NDKFDKLYIWGVHHPSTDSEQTSLYVQAIGRVTVSTKSSQQTVIPNIGSRPWVRGISSRISI

YWTIVKPGDILLISSTGNLIAPRGYFKIRNGKSSIMRSDAPIDNCYSECITPNGSIPNDKPF

QNVNRITYGACPKYVKQKTLKLATGMRNVPEKQTRGIFGAIAGFIENGWEGMVDGWYGFRHQ

NSEGTGQAADLKSTQAAIDQVNGKLNRLIEKTNEKFHQIEKEFSEVEGRIQDLEKYVEDTKI

DLWSYNAELLVALENQHTIDLTDSEMNKLFEKTRKQLRENAEDMGNGCFKIYHKCDNACIGS

IRNGTYDHDVYRDEALNNRFQIKGVELKSGYKDWILWISFAISCFLLCVVLLGFIMWACQKG

NIRCNICI

Nucleotide Sequence of NA of H1N1
(A/swine/Minnesota/37866/1999):

SEQ ID NO: 5

```
   1  TATTGGTCTC AGGGAGCAAA AGCAGGAGTt taaaatgaat acaaatcaaa gaataataac
  61  catagggaca gtctgtctga tagtcggaat agttagtcta ttattgcaga tagggaatat
 121  agtctcatta tggataagcc attcaattca gactggagaa aaaaaccact ctgagatatg
 181  caatcaaaac gtcattacat atgaaaataa cacatgggtg aaccaaactt atgtaaacat
 241  tagcaacacc aacattgctg atggacaggg cgtgacttca ataaaactag ccggcaattc
 301  ctctctttgc ccaataagtg ggtgggctat atatagcaaa gacaatagca taaggattgg
 361  ttccaaagga gatattttg tcataagaga accattcatt tcatgctctc atttggaatg
 421  caggactttt tttctgaccc aaggtgcttt gctgaatgac aggcattcta atggaaccgt
 481  caaggacagg agcccttata gaaccttaat gagctgccca attggtgaag ctccatctcc
 541  gtacaattca aggttcgaat cagttgcttg gtcagcaagt gcatgccatg atggaatggg
 601  atggctaaca atcgggattt ccggtccaga taatggagca gtggcggttt gaaatacaa
 661  tggtataata acagatacaa taaaaagttg gagaaacaaa atactaagaa cacaagagtc
 721  agaatgtgtt tgtataaacg gttcatgttt tactataatg actgatggcc caagcaatgg
 781  gcaggcctca tacaaaatat tcaaaatgga gaaagggaag attattaagt cagttgagct
 841  ggatgcaccc aattaccatt atgaggaatg ctcttgttac cctgatacag caaagtgat
 901  gtgtgtgtgc agagacaatt ggcatgcttc gaatcgacca tgggtctctt tcgaccggaa
 961  tcttgattat cagataggggt acatatgcag tggggttttc ggtgataacc cgcgttctaa
1021  tgatgggaaa ggcaattgtg gcccagtact ttctaatgga gcaaatggag tgaaaggatt
1081  ctcattcaga tatggcaatg gtgtttggat aggaagaact aaaagtatca gttctagaag
1141  tggatttgag atgatttggg atccaaatgg atggacggaa actgatagta gttctctat
1201  aaagcaggat attatagcat taactgactg gtcaggatac agtgggagtt tgtccaaca
1261  tcctgagtta acaggaatga actgcataaa gccttgtttc tgggtagagt taattagagg
1321  acaacccaag gagagcacaa tctggactag tggaagcagc atttctttct gtggtgtgga
1381  cagtgaaacc gcaagctggt catggccaga cggagctgat ctgccattca ccattgacaa
1441  gtagtctgtt cAAAAAACTC CTTGTTTCTA CTAATACGAG ACCATAT
```

Nucleotide Sequence of HA of H1N1
(A/swine/Minnesota/37866/1999):

SEQ ID NO: 6

```
   1  TATTCGTCTC AGGGAGCAAA AGCAGGGGaa aataaaagca actagaatga aggcaatact
  61  agtagtcttg ctatatgcat ttacaaccgc aaatgcagac acattatgta taggttatca
 121  tgcaaataat tcaactgaca ctgttgacac agtactagaa aagaatgtaa cagtaacaca
 181  ctctgttaac cttctagaag aaaaacataa cgggaaacta tgtaaactaa gaggagtagc
 241  cccattgcat ttgggtaaat gtaacattgc tggatggatc ctgggaaatc cagagtgtga
 301  atcactattc acagcaagct catggtctta cattgtggaa acatctaatt cagacaatgg
 361  gacatgttac ccaggagatt tcatcaatta tgaagagcta agagagcagt gagctcagt
 421  gtcatcattt gaaagatttg agatattccc caaggcaagt tcatggccca attatgaaac
 481  aagcagaggt gtgacggcag catgtcctta tgctggagca aacagcttct acagaaattt
 541  aatatggctg gtaaaaaag gaaattcata cccaaagctc agcaaatctt atattaacaa
 601  taaggagaag gaagtcctcg tgctataggg cattcaccat ccatctacta gtactgacca
 661  acaaagtctc taccagaatg cagatgccta tgttttgta ggatcatcaa aatacagcaa
```

-continued

```
 721    gaaattcaag ccagaaatag caacaagacc caaagtgagg gaccaagcag ggagaatgaa
 781    ctattactgg acactagtag agcctggaga cacaataaca ttcgaagcaa ccggaaatct
 841    agtggtacca agatatgcct tcgcaatgaa gagaggctct ggatctggta ttatcatttc
 901    agatacatca gtccacgatt gcaatacgaa ttgtcaaaca cccaaaggtg ctataaacac
 961    cagtcttcca tttcagaaca tacatccagt cacaatagga gaatgtccga aatatgtcaa
1021    aagcaaaaaa ttgagaatgg ctacaggatt aaggaatatc ccgtccattc aatctagagg
1081    cctgtttgga gccattgctg gctttattga gggggggatgg acaggaatga tagatggatg
1141    gtacggttat caccatcaaa atgagcaggg atcaggatat gcagccgacc gaaaaagcac
1201    acagagtgcc attgacggga tcactaacaa ggtaaattct attattgaaa agatgaactc
1261    acaattcaca gcagtgggca agaattcaa ccacctggaa aagagaatag agaatttgaa
1321    cagaaaggtt gatgatggtt ttctggatgt ttggacttac aatgccgagc tgttggttct
1381    gttggaaaat gaaggactt tggattatca cgattcaaat gtgaagaacc tatatgaaaa
1441    agtaagaagc cagctaaaaa acaatgccaa ggaaattgga aatggctgct ttgaatttta
1501    ccacaaatgt gatgacacat gcatggagag cgtcaaaaat gggacttatg attacccaaa
1561    atactcagaa gaagcaaaac taaacagaga ggagatagat ggggtaaagc tggaatcaac
1621    agaggtttac cagatttttgg cgatctattc aactgtcgcc agttcattgg tactgttagt
1681    ctccctgggg gcaatcagct tctggatgtg ctccaatggg tctttacagt gcagaatatg
1741    tatttaaaat tgggatttca gaggcatgag aAAAACACCC TTGTTTCTAC TAATACGAGA
1801    CGATAT
```

Amino Acid Sequence of NA of H1N1
(A/swine/Minnesota/37866/1999):

SEQ ID NO: 7

MNTNQRIITIGTVCLIVGIVSLLLQIGNIVSLWISHSIQTGEKNHSEICNQNVITYENNTWV

NQTYVNISNTNIADGQGVTSIKLAGNSSLCPISGWAIYSKDNSIRIGSKGDIFVIREPFISC

SHLECRTFFLTQGALLNDRHSNGTVKDRSPYRTLMSCPIGEAPSPYNSRFESVAWSASACHD

GMGWLTIGISGPDNGAVAVLKYNGIITDTIKSWRNKILRTQESECVCINGSCFTIMTDGPSN

GQASYKIFKMEKGKIIKSVELDAPNYHYEECSCYPDTGKVMCVCRDNWHASNRPWVSFDRNL

DYQIGYICSGVFGDNPRSNDGKGNCGPVLSNGANGVKGFSFRYGNGVWIGRTKSISSRSGFE

MIWDPNGWTETDSSFSIKQDIIALTDWSGYSGSFVQHPELTGMNCIKPCFWVELIRGQPKES

TIWTSGSSISFCGVDSETASWSWPDGADLPFTIDK

Amino Acid Sequence of HA of H1N1
(A/swine/Minnesota/37866/1999):

SEQ ID NO: 8

MKAILVVLLYAFTTANADTLCIGYHANNSTDTVDTVLEKNVTVTHSVNLLEEKHNGKLCKLR

GVAPLHLGKCNIAGWILGNPECESLFTASSWSYIVETSNSDNGTCYPGDFINYEELREQLSS

VSSFERFEIFPKASSWPNYETSRGVTAACPYAGANSFYRNLIWLVKKGNSYPKLSKSYINNK

EKEVLVLWGIHHPSTSTDQQSLYQNADAYVFVGSSKYSKKFKPEIATRPKVRDQAGRMNYYW

TLVEPGDTITFEATGNLVVPRYAFAMKRGSGSGIIISDTSVHDCNTNCQTPKGAINTSLPFQ

NIHPVTIGECPKYVKSKKLRMATGLRNIPSIQSRGLFGAIAGFIEGGWTGMIDGWYGYHHQN

EQGSGYAADRKSTQSAIDGITNKVNSIIEKMNSQFTAVGKEFNHLEKRIENLNRKVDDGFLD

VWTYNAELLVLLENERTLDYHDSNVKNLYEKVRSQLKNNAKEIGNGCFEFYHKCDDTCMESV

KNGTYDYPKYSEEAKLNREEIDGVKLESTEVYQILAIYSTVASSLVLLVSLGAISFWMCSNG

SLQCRICI

The invention claimed is:

1. An immunogenic composition comprising:
   a) a modified live H3 virus of H3N2 swine influenza, wherein the modified live H3 virus is attenuated by truncating the NS1 protein and the modified live H3 virus comprises a carboxy-terminal truncated NS1 protein consisting of NS1 amino acids 1 through 124, 125, 126, 127 or 128; and
   b) a modified live H1 virus of H1N1 swine influenza, wherein the modified live H1 virus is attenuated by truncating the NS1 protein and the modified live H3 virus comprises a carboxy-terminal truncated NS1 protein consisting of NS1 amino acids 1 through 124, 125, 126, 127 or 128.

2. The immunogenic composition of claim 1, wherein the H3 and H1 viruses each comprise a carboxy-terminal truncated NS1 protein consisting of NS1 amino acids 1 through 126.

3. The immunogenic composition of claim 1, wherein the H3 virus comprises a protein having 95% or greater sequence identity to SEQ ID NO: 3 or 4.

4. The immunogenic composition of claim 1, wherein the H1 virus comprises a protein having 95% or greater sequence identity to SEQ ID NO: 7 or 8.

5. The immunogenic composition of claim 1, wherein the H3 virus comprises a protein having 95% or greater sequence identity to SEQ ID NO: 3 or 4, and wherein the H1 virus comprises a protein having 95% or greater sequence identity to SEQ ID NO: 7 or 8.

6. The immunogenic composition of claim 1, wherein the modified live H3 and H1 viruses synergistically induce a protective immunize response in an animal against swine influenza.

7. The immunogenic composition of claim 1, wherein the immunogenic composition has between 1 to 4 $\log_{10}$ of each of the modified live H3 and H1 viruses.

8. A method for inducing protective immunity in an animal against swine influenza comprising:
   administering to the animal a modified live H3 virus of H3N2 swine influenza and a modified live H1 virus of H1N1 swine influenza, wherein the modified live H3 and H1 viruses are attenuated by truncating the NS1 proteins of the live H3 and H1 viruses and wherein the modified live H3 and H1 viruses each comprise a carboxy-terminal truncated NS1 protein consisting of NS1 amino acids 1 through 124, 125, 126, 127 or 128.

9. The method of claim 8, wherein the modified live H3 and H1 viruses are administered in a single dose.

10. The method of claim 8, wherein the animal is a swine, cattle, cat, or dog.

11. The method of claim 8, wherein the animal is a swine.

12. The method of claim 8, wherein the modified live H3 and H1 viruses are administered intranasally.

13. The method of claim 8, wherein the animal is a pregnant or lactating sow.

14. The method of claim 8, wherein the animal is month old or less.

15. The method of claim 8, wherein the animal is two weeks old or less.

16. The method of claim 8, wherein the animal is one week old or less.

17. The method of claim 8, wherein the animal has circulating maternal antibodies against swine influenza.

18. The method of claim 8, wherein the H3 and H1 viruses each comprise a carboxy-terminal truncated NS1 protein consisting of NS1 amino acids 1 through 126.

19. The method of claim 8, wherein the H3 virus comprises a protein having 95% or greater sequence identity to SEQ ID NO: 3 or 4.

20. The method of claim 8, wherein the H1 virus comprises a protein having 95% or greater sequence identity to SEQ ID NO: 7 or 8.

21. The method of claim 8, wherein the H3 virus comprises a protein having 95% or greater sequence identity to SEQ ID NO: 3 or 4, and wherein the H1 virus comprises a protein having 95% or greater sequence identity to SEQ ID NO: 7 or 8.

22. The method of claim 8, wherein the modified live H3 and H1 viruses synergistically induce a protective immunize response in the animal against swine influenza.

23. The method of claim 8, wherein between 1 to 4 $\log_{10}$ of each of the modified live H3 and H1 viruses is administered to the animal.

24. The method of claim 8, wherein between 2 to 4 $\log_{10}$ of each of the modified live H3 and H1 viruses is administered to the animal.

25. The method of claim 8, wherein the H3 virus comprises a polynucleotide having 95% or greater sequence identity to a complementary sequence of SEQ ID NO: 1 or 2.

26. The method of claim 8, wherein the H1 virus comprises a polynucleotide having 95% or greater sequence identity to a complementary sequence of SEQ ID NO: 5 or 6.

* * * * *

SEQUENCE LISTING

<160> NUMBER OF SEQ ID NOS: 8

<210> SEQ ID NO 1
<211> LENGTH: 1496
<212> TYPE: DNA
<213> ORGANISM: swine influenza virus

<400> SEQUENCE: 1

| | | | | | |
|---|---|---|---|---|---|
| tattggtctc | agggagcaaa | agcaggagta | aagatgaatc | caaatcaaaa | gataataacg | 60 |
| attggctctg | tttctctcac | tattgccaca | atgtgcttcc | ttatgcaaat | tgccatcctg | 120 |
| gtaactactg | taacattgca | tttcaagcaa | tatgaatgca | actaccccc | aaacaaccaa | 180 |
| gtaatactgt | gtgaaccaac | aataatagaa | agaaacataa | cagagatagt | gtatctgacc | 240 |
| aacaccacca | tagagaagga | aatatgcccc | aaactagcag | aatacagaaa | ttggtcaaag | 300 |
| ccgcaatgta | aaattacagg | atttgcacct | ttttccaagg | acaattcgat | taggcttttcc | 360 |
| gctggtgggg | acatttgggt | gacaagagaa | ccttatgtgt | catgcgatcc | tgacaagtgt | 420 |
| tatcaatttg | cccttggaca | gggaacaaca | ctaaacaaca | ggcattcaaa | tgacacagta | 480 |
| catgatagga | ccccttatcg | aaccctattg | atgaatgagt | tgggtgttcc | atttcatttg | 540 |
| ggaaccaagc | aagtgtgcat | agcatggtcc | agctcaagtt | gtcacgatgg | aaaagcatgg | 600 |
| ctgcatgttt | gtgtaactgg | gcatgatgaa | atgcaactg | ctagcttcat | ttacgatggg | 660 |
| aggcttgtag | atagtattgg | ttcatggtcc | aaaaaaatcc | tcaggaccca | ggagtcggaa | 720 |
| tgcgttttgta | tcaatggaac | ttgtacagta | gtaatgactg | atgggagtgc | ttcaggaaga | 780 |
| gctgatacta | aaatattatt | cattgaggag | gggaaaatcg | ttcatattag | cccattgtta | 840 |
| ggaagtgctc | agcatgtcga | ggagtgctcc | tgttatcctc | gatatcctgg | tgtcagatgt | 900 |
| gtctgcagag | acaactggaa | aggctccaat | aggcccatcg | tagatataaa | tgtaaaggat | 960 |
| tatagcattg | tttccagtta | tgtgtgctca | ggacttgttg | gagacacacc | cagaaaaaac | 1020 |
| gacagatcca | gcagtagcaa | ttgcctgaat | cctaacaatg | aggaagggg | tcatggagtg | 1080 |
| aaaggctggg | cctttgatga | tggaaatgac | gtgtggatgg | gaagaacgat | caacgagaag | 1140 |
| ttacgctcag | gttatgaaac | cttcaaagtc | attgaaggct | ggtccaaacc | taactccaaa | 1200 |
| ttgcagataa | ataggcaagt | catagttgac | agaggtgata | ggtccggtta | ttctggcatt | 1260 |
| ttctctgttg | aaggcaaaag | ctgcatcaat | cggtgctttt | atgtggagtt | gataagggga | 1320 |
| aggaaacagg | aaactgaagt | atggtggacc | tcaaacagta | ttgttgtgtt | ttgtggcacc | 1380 |
| tcaggtacat | atggaacagg | ctcatggcct | gatgggcgg | acatcaatct | catgcctata | 1440 |
| taagctttcg | caattttaga | aaaaaactcc | ttgtttctac | taatacgaga | ccatat | 1496 |

<210> SEQ ID NO 2
<211> LENGTH: 1791
<212> TYPE: DNA
<213> ORGANISM: swine influenza virus

<400> SEQUENCE: 2

| | | | | | |
|---|---|---|---|---|---|
| tattcgtctc | agggagcaaa | agcaggggat | aattctatta | accatgaaga | ctatcattgc | 60 |
| tttgagctac | attttatgtc | tggttttcgc | tcaaaaactt | cccggaaatg | acaacagcac | 120 |
| agcaacgctg | tgcctgggac | accatgcagt | gccaaacgga | accctagtga | aaacaatcac | 180 |
| gaatgatcaa | attgaagtga | ctaatgctac | tgagctggtt | cagagttcct | caacaggtag | 240 |
| aatatgcgac | agtcctcacc | gaatccttga | tggaaaaaac | tgcacattga | tagatgctct | 300 |
| actgggagac | cctcattgcg | atggctttca | aaataaggaa | tgggacctttt | ttattgaacg | 360 |

-continued

```
cagcaaagct tacagcaact gttaccctta tgatgtgccg gattattcct cccttaggtc    420
actagttgcc tcatcaggca ccctggagtt taccaatgaa gacttcaatt ggactggggt    480
cgctcaggat gggggaagct attcttgcaa aaggggatct gttaaaagtt tctttagtag    540
attgaattgg ttacacaaat tagaatacaa atatccagca ctgaacgtga ctatgccaaa    600
caatgacaaa tttgacaaat tgtacatttg gggggttcac cacccgagca cggacagtga    660
acaaaccagc ctgtatgttc aagcaatagg gagagtcaca gtctctacca aaagtagcca    720
acaaactgta atcccgaaca tcgggtccag accctgggtg aggggcatct ccagtagaat    780
aagcatctat tggacaatag taaaaccggg agacatactt ttgattagca gcacagggaa    840
tctaattgct cctcggggtt acttcaaaat acgaaatggg aaaagctcaa taatgaggtc    900
agatgcaccc attgacaact gctattctga atgcatcact ccaaatggaa gcattcccaa    960
tgacaaacct tttcaaaatg taaataggat cacatatggg gcctgtccca aatatgttaa   1020
gcaaaaaacc ctgaaattgg caacagggat gcggaatgta ccagagaaac aaactagagg   1080
catattcggc gcaatcgcag gtttcataga aaatggttgg gagggaatgg tagacggttg   1140
gtacggtttc aggcatcaaa attctgaggg cacaggacaa gcagcagatc ttaaaagcac   1200
ccaagcagca atcgatcaag tcaacgggaa attgaatagg ttaatcgaga aaacgaacga   1260
gaaattccat caaatcgaaa aagaattttc agaagtagaa gggagaattc aggacctcga   1320
gaaatatgtt gaagacacta aaatagatct ctggtcttac aacgcggagc tccttgttgc   1380
cctggagaat caacatacaa ttgatctaac tgactcagaa atgaacaaac tgtttgaaaa   1440
aacaaggaag caactgaggg aaaatgctga ggacatgggc aatggttgct tcaaaatata   1500
ccacaaatgt gacaatgcct gcatagggtc aatcagaaat ggaacttatg accatgatgt   1560
atacagagac gaagcattaa acaaccggtt ccagatcaaa ggtgttgagc tgaaatcagg   1620
atacaaagat tggatcctat ggatttcctt tgccatatca tgctttttgc tttgtgttgt   1680
tttgctgggg ttcatcatgt gggcctgcca aaaaggcaac attaggtgca acatttgcat   1740
ttgagtgcat taattaaaaa caccc ttgtt tctactaata cgagacgata t           1791
```

<210> SEQ ID NO 3
<211> LENGTH: 469
<212> TYPE: PRT
<213> ORGANISM: swine influenza virus

<400> SEQUENCE: 3

```
Met Asn Pro Asn Gln Lys Ile Ile Thr Ile Gly Ser Val Ser Leu Thr
1               5                   10                  15

Ile Ala Thr Met Cys Phe Leu Met Gln Ile Ala Ile Leu Val Thr Thr
            20                  25                  30

Val Thr Leu His Phe Lys Gln Tyr Glu Cys Asn Tyr Pro Pro Asn Asn
        35                  40                  45

Gln Val Ile Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
```

```
            115                 120                 125
Cys Tyr Gln Phe Ala Leu Gly Gln Gly Thr Thr Leu Asn Asn Arg His
130                 135                 140
Ser Asn Asp Thr Val His Asp Arg Thr Pro Tyr Arg Thr Leu Leu Met
145                 150                 155                 160
Asn Glu Leu Gly Val Pro Phe His Leu Gly Thr Lys Gln Val Cys Ile
                165                 170                 175
Ala Trp Ser Ser Ser Cys His Asp Gly Lys Ala Trp Leu His Val
            180                 185                 190
Cys Val Thr Gly His Asp Glu Asn Ala Thr Ala Ser Phe Ile Tyr Asp
            195                 200                 205
Gly Arg Leu Val Asp Ser Ile Gly Ser Trp Ser Lys Lys Ile Leu Arg
        210                 215                 220
Thr Gln Glu Ser Glu Cys Val Cys Ile Asn Gly Thr Cys Thr Val Val
225                 230                 235                 240
Met Thr Asp Gly Ser Ala Ser Gly Arg Ala Asp Thr Lys Ile Leu Phe
                245                 250                 255
Ile Glu Glu Gly Lys Ile Val His Ile Ser Pro Leu Leu Gly Ser Ala
            260                 265                 270
Gln His Val Glu Glu Cys Ser Cys Tyr Pro Arg Tyr Pro Gly Val Arg
        275                 280                 285
Cys Val Cys Arg Asp Asn Trp Lys Gly Ser Asn Arg Pro Ile Val Asp
290                 295                 300
Ile Asn Val Lys Asp Tyr Ser Ile Val Ser Ser Tyr Val Cys Ser Gly
305                 310                 315                 320
Leu Val Gly Asp Thr Pro Arg Lys Asn Asp Arg Ser Ser Ser Ser Asn
                325                 330                 335
Cys Leu Asn Pro Asn Asn Glu Glu Gly Gly His Gly Val Lys Gly Trp
            340                 345                 350
Ala Phe Asp Asp Gly Asn Asp Val Trp Met Gly Arg Thr Ile Asn Glu
        355                 360                 365
Lys Leu Arg Ser Gly Tyr Glu Thr Phe Lys Val Ile Glu Gly Trp Ser
370                 375                 380
Lys Pro Asn Ser Lys Leu Gln Ile Asn Arg Gln Val Ile Val Asp Arg
385                 390                 395                 400
Gly Asp Arg Ser Gly Tyr Ser Gly Ile Phe Ser Val Glu Gly Lys Ser
                405                 410                 415
Cys Ile Asn Arg Cys Phe Tyr Val Glu Leu Ile Arg Gly Arg Lys Gln
            420                 425                 430
Glu Thr Glu Val Trp Trp Thr Ser Asn Ser Ile Val Val Phe Cys Gly
        435                 440                 445
Thr Ser Gly Thr Tyr Gly Thr Gly Ser Trp Pro Asp Gly Ala Asp Ile
450                 455                 460
Asn Leu Met Pro Ile
465

<210> SEQ ID NO 4
<211> LENGTH: 566
<212> TYPE: PRT
<213> ORGANISM: swine influenza virus

<400> SEQUENCE: 4

Met Lys Thr Ile Ile Ala Leu Ser Tyr Ile Leu Cys Leu Val Phe Ala
1               5                   10                  15
```

```
Gln Lys Leu Pro Gly Asn Asp Asn Ser Thr Ala Thr Leu Cys Leu Gly
             20                  25                  30

His His Ala Val Pro Asn Gly Thr Leu Val Lys Thr Ile Thr Asn Asp
         35                  40                  45

Gln Ile Glu Val Thr Asn Ala Thr Glu Leu Val Gln Ser Ser Ser Thr
     50                  55                  60

Gly Arg Ile Cys Asp Ser Pro His Arg Ile Leu Asp Gly Lys Asn Cys
 65                  70                  75                  80

Thr Leu Ile Asp Ala Leu Leu Gly Asp Pro His Cys Asp Gly Phe Gln
                 85                  90                  95

Asn Lys Glu Trp Asp Leu Phe Ile Glu Arg Ser Lys Ala Tyr Ser Asn
            100                 105                 110

Cys Tyr Pro Tyr Asp Val Pro Asp Tyr Ser Ser Leu Arg Ser Leu Val
        115                 120                 125

Ala Ser Ser Gly Thr Leu Glu Phe Thr Asn Glu Asp Phe Asn Trp Thr
    130                 135                 140

Gly Val Ala Gln Asp Gly Gly Ser Tyr Ser Cys Lys Arg Gly Ser Val
145                 150                 155                 160

Lys Ser Phe Phe Ser Arg Leu Asn Trp Leu His Lys Leu Glu Tyr Lys
                165                 170                 175

Tyr Pro Ala Leu Asn Val Thr Met Pro Asn Asn Asp Lys Phe Asp Lys
        180                 185                 190

Leu Tyr Ile Trp Gly Val His His Pro Ser Thr Asp Ser Glu Gln Thr
    195                 200                 205

Ser Leu Tyr Val Gln Ala Ile Gly Arg Val Thr Val Ser Thr Lys Ser
    210                 215                 220

Ser Gln Gln Thr Val Ile Pro Asn Ile Gly Ser Arg Pro Trp Val Arg
225                 230                 235                 240

Gly Ile Ser Ser Arg Ile Ser Ile Tyr Trp Thr Ile Val Lys Pro Gly
                245                 250                 255

Asp Ile Leu Leu Ile Ser Ser Thr Gly Asn Leu Ile Ala Pro Arg Gly
        260                 265                 270

Tyr Phe Lys Ile Arg Asn Gly Lys Ser Ser Ile Met Arg Ser Asp Ala
    275                 280                 285

Pro Ile Asp Asn Cys Tyr Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Lys Tyr Val Lys Gln Lys Thr Leu Lys Leu Ala Thr Gly Met
                325                 330                 335

Arg Asn Val Pro Glu Lys Gln Thr Arg Gly Ile Phe Gly Ala Ile Ala
        340                 345                 350

Gly Phe Ile Glu Asn Gly Trp Glu Gly Met Val Asp Gly Trp Tyr Gly
    355                 360                 365

Phe Arg His Gln Asn Ser Glu Gly Thr Gly Gln Ala Ala Asp Leu Lys
    370                 375                 380

Ser Thr Gln Ala Ala Ile Asp Gln Val Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
        420                 425                 430

Lys Ile Asp Leu Trp Ser Tyr Asn Ala Glu Leu Leu Val Ala Leu Glu
```

```
                    435                 440                 445
Asn Gln His Thr Ile Asp Leu Thr Asp Ser Glu Met Asn Lys Leu Phe
    450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Val Leu Leu Gly Phe Ile Met Trp Ala Cys Gln Lys Gly Asn Ile
545                 550                 555                 560

Arg Cys Asn Ile Cys Ile
                565
```

<210> SEQ ID NO 5
<211> LENGTH: 1487
<212> TYPE: DNA
<213> ORGANISM: swine influenza virus

<400> SEQUENCE: 5

```
tattggtctc agggagcaaa agcaggagtt aaaatgaat acaaatcaaa gaataataac      60
catagggaca gtctgtctga tagtcggaat agttagtcta ttattgcaga tagggaatat    120
agtctcatta tggataagcc attcaattca gactggagaa aaaaaccact ctgagatatg    180
caatcaaaac gtcattacat atgaaaataa cacatgggtg aaccaaactt atgtaaacat    240
tagcaacacc aacattgctg atggacaggg cgtgacttca ataaaactag ccggcaattc    300
ctctctttgc ccaataagtg ggtgggctat atatagcaaa gacaatagca taaggattgg    360
ttccaaagga gatattttg tcataagaga accattcatt tcatgctctc atttggaatg    420
caggactttt tttctgaccc aaggtgcttt gctgaatgac aggcattcta atggaaccgt    480
caaggacagg agcccttata gaaccttaat gagctgccca attggtgaag ctccatctcc    540
gtacaattca aggttcgaat cagttgcttg gtcagcaagt gcatgccatg atggaatggg    600
atggctaaca atcgggattt ccggtccaga taatggagca gtggcggttt tgaaatacaa    660
tggtataata acagatacaa taaaaagttg gagaaacaaa atactaagaa cacaagagtc    720
agaatgtgtt tgtataaacg gttcatgttt tactataatg actgatggcc aagcaatgg    780
gcaggcctca tacaaaatat tcaaaatgga gaagggaag attattaagt cagttgagct    840
ggatgcaccc aattaccatt atgaggaatg ctcttgttac cctgatacag caaagtgat    900
gtgtgtgtgc agagacaatt ggcatgcttc gaatcgacca tggtctctt tcgaccggaa    960
tcttgattat cagatagggt acatatgcag tggggttttc ggtgataacc cgcgttctaa  1020
tgatgggaaa ggcaattgtg cccagtact ttctaatgga gcaaatggag tgaaaggatt   1080
ctcattcaga tatggcaatg gtgtttggat aggaagaact aaaagtatca gttctagaag  1140
tggatttgag atgatttggg atccaaatgg atggacggaa actgatagta gtttctctat  1200
aaagcaggat attatagcat taactgactg gtcaggatac agtgggagtt ttgtccaaca  1260
tcctgagtta acaggaatga actgcataaa gccttgtttc tgggtagagt taattagagg  1320
acaacccaag gagagcacaa tctggactag tggaagcagc atttctttct gtggtgtgga  1380
```

```
cagtgaaacc gcaagctggt catggccaga cggagctgat ctgccattca ccattgacaa    1440
gtagtctgtt caaaaaactc cttgtttcta ctaatacgag accatat                  1487

<210> SEQ ID NO 6
<211> LENGTH: 1806
<212> TYPE: DNA
<213> ORGANISM: swine influenza virus

<400> SEQUENCE: 6
tattcgtctc agggagcaaa agcaggggaa aataaaagca actagaatga aggcaatact     60
agtagtcttg ctatatgcat ttacaaccgc aaatgcagac acattatgta taggttatca    120
tgcaaataat tcaactgaca ctgttgacac agtactagaa aagaatgtaa cagtaacaca    180
ctctgttaac cttctagaag aaaaacataa cggaaaacta tgtaaactaa gaggagtagc    240
cccattgcat ttgggtaaat gtaacattgc tggatggatc ctgggaaatc cagagtgtga    300
atcactattc acagcaagct catggtctta cattgtggaa acatctaatt cagacaatgg    360
gacatgttac ccaggagatt tcatcaatta tgaagagcta agagagcagt tgagctcagt    420
gtcatcattt gaaagatttg agatattccc caaggcaagt tcatggccca attatgaaac    480
aagcagaggt gtgacggcag catgtcctta tgctggagca aacagcttct acagaaattt    540
aatatggctg gtaaaaaaag gaaattcata cccaaagctc agcaaatctt atattaacaa    600
taaggagaag gaagtcctcg tgctatgggg cattcaccat ccatctacta gtactgacca    660
acaaagtctc taccagaatg cagatgccta tgtttttgta ggatcatcaa atacagcaa     720 gaaattcaag ccagaaatag caacaagacc caaagtgagg gaccaagcag ggagaatgaa    780
ctattactgg acactagtag agcctggaga cacaataaca ttcgaagcaa ccggaaatct    840
agtggtacca agatatgcct tcgcaatgaa gagaggctct ggatctggta ttatcatttc    900
agatacatca gtccacgatt gcaatacgaa ttgtcaaaca cccaaggtg ctataaacac    960 cagtcttcca tttcagaaca tacatccagt cacaatagga gaatgtccga aatatgtcaa   1020
aagcaaaaaa ttgagaatgg ctacaggatt aaggaatatc ccgtccattc aatctagagg   1080
cctgtttgga gccattgctg gctttattga gggggatgg acaggaatga tagatggatg   1140
gtacggttat caccatcaaa atgagcaggg atcaggatat gcagccgacc gaaaaagcac   1200
acagagtgcc attgacggga tcactaacaa ggtaaattct attattgaaa agatgaactc   1260
acaattcaca gcagtgggca agaattcaa ccacctggaa agagaataga gaatttgaa    1320 cagaaaggtt gatgatggtt ttctggatgt ttggactac aatgccgagc tgttggttct   1380
gttggaaaat gaaaggactt tggattatca cgattcaaat gtgaagaacc tatatgaaaa   1440
agtaagaagc cagctaaaaa acaatgccaa ggaaattgga aatggctgct ttgaatttta   1500
ccacaaatgt gatgacacat gcatggagag cgtcaaaaat gggacttatg attacccaaa   1560
atactcagaa gaagcaaaac taaacagaga ggagatagat gggtaaagc tggaatcaac   1620 agaggtttac cagattttgg cgatctattc aactgtcgcc agttcattgg tactgttagt   1680
ctccctgggg gcaatcagct tctggatgtg ctccaatggg tctttacagt gcagaatatg   1740
tatttaaaat tgggatttca gaggcatgag aaaaacaccc ttgtttctac taatacgaga   1800
cgatat                                                             1806

<210> SEQ ID NO 7
<211> LENGTH: 469
<212> TYPE: PRT
```

-continued

<213> ORGANISM: swine influenza virus

<400> SEQUENCE: 7

Met Asn Thr Asn Gln Arg Ile Ile Thr Ile Gly Thr Val Cys Leu Ile
1               5                   10                  15

Val Gly Ile Val Ser Leu Leu Leu Gln Ile Gly Asn Ile Val Ser Leu
            20                  25                  30

Trp Ile Ser His Ser Ile Gln Thr Gly Glu Lys Asn His Ser Glu Ile
        35                  40                  45

Cys Asn Gln Asn Val Ile Thr Tyr Glu Asn Asn Thr Trp Val Asn Gln
    50                  55                  60

Thr Tyr Val Asn Ile Ser Asn Thr Asn Ile Ala Asp Gly Gln Gly Val
65                  70                  75                  80

Thr Ser Ile Lys Leu Ala Gly Asn Ser Ser Leu Cys Pro Ile Ser Gly
                85                  90                  95

Trp Ala Ile Tyr Ser Lys Asp Asn Ser Ile Arg Ile Gly Ser Lys Gly
            100                 105                 110

Asp Ile Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Arg His
    130                 135                 140

Ser Asn Gly Thr Val Lys Asp Arg Ser Pro Tyr Arg Thr Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Glu Ser Glu Cys Val Cys Ile Asn Gly Ser Cys Phe Thr
225                 230                 235                 240

Ile Met Thr Asp Gly Pro Ser Asn Gly Gln Ala Ser Tyr Lys Ile Phe
                245                 250                 255

Lys Met Glu Lys Gly Lys Ile Ile Lys Ser Val Glu Leu Asp Ala Pro
            260                 265                 270

Asn Tyr His Tyr Glu Glu Cys Ser Cys Tyr Pro Asp Thr Gly Lys Val
        275                 280                 285

Met Cys Val Cys Arg Asp Asn Trp His Ala Ser Asn Arg Pro Trp Val
    290                 295                 300

Ser Phe Asp Arg Asn Leu Asp Tyr Gln Ile Gly Tyr Ile Cys Ser Gly
305                 310                 315                 320

Val Phe Gly Asp Asn Pro Arg Ser Asn Asp Gly Lys Gly Asn Cys Gly
                325                 330                 335

Pro Val Leu Ser Asn Gly Ala Asn Gly Val Lys Gly Phe Ser Phe Arg
            340                 345                 350

Tyr Gly Asn Gly Val Trp Ile Gly Arg Thr Lys Ser Ile Ser Ser Arg
        355                 360                 365

Ser Gly Phe Glu Met Ile Trp Asp Pro Asn Gly Trp Thr Glu Thr Asp
370                 375                 380

Ser Ser Phe Ser Ile Lys Gln Asp Ile Ile Ala Leu Thr Asp Trp Ser
385                 390                 395                 400

```
Gly Tyr Ser Gly Ser Phe Val Gln His Pro Glu Leu Thr Gly Met Asn
                405                 410                 415

Cys Ile Lys Pro Cys Phe Trp Val Glu Leu Ile Arg Gly Gln Pro Lys
            420                 425                 430

Glu Ser Thr Ile Trp Thr Ser Gly Ser Ser Ile Ser Phe Cys Gly Val
        435                 440                 445

Asp Ser Glu Thr Ala Ser Trp Ser Trp Pro Asp Gly Ala Asp Leu Pro
    450                 455                 460

Phe Thr Ile Asp Lys
465

<210> SEQ ID NO 8
<211> LENGTH: 566
<212> TYPE: PRT
<213> ORGANISM: swine influenza virus

<400> SEQUENCE: 8

Met Lys Ala Ile Leu Val Val Leu Leu Tyr Ala Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Glu Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Phe Thr Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Ala Ser Ser Trp Pro Asn Tyr Glu
    130                 135                 140

Thr Ser Arg Gly Val Thr Ala Ala Cys Pro Tyr Ala Gly Ala Asn Ser
145                 150                 155                 160

Phe Tyr Arg Asn Leu Ile Trp Leu Val Lys Lys Gly Asn Ser Tyr Pro
                165                 170                 175

Lys Leu Ser Lys Ser Tyr Ile Asn Asn Lys Glu Lys Glu Val Leu Val
            180                 185                 190

Leu Trp Gly Ile His His Pro Ser Thr Ser Thr Asp Gln Gln Ser Leu
        195                 200                 205

Tyr Gln Asn Ala Asp Ala Tyr Val Phe Val Gly Ser Ser Lys Tyr Ser
    210                 215                 220

Lys Lys Phe Lys Pro Glu Ile Ala Thr Arg Pro Lys Val Arg Asp Gln
225                 230                 235                 240

Ala Gly Arg Met Asn Tyr Tyr Trp Thr Leu Val Glu Pro Gly Asp Thr
                245                 250                 255

Ile Thr Phe Glu Ala Thr Gly Asn Leu Val Val Pro Arg Tyr Ala Phe
            260                 265                 270

Ala Met Lys Arg Gly Ser Gly Ser Gly Ile Ile Ile Ser Asp Thr Ser
        275                 280                 285

Val His Asp Cys Asn Thr Asn Cys Gln Thr Pro Lys Gly Ala Ile Asn
    290                 295                 300
```

-continued

```
Thr Ser Leu Pro Phe Gln Asn Ile His Pro Val Thr Ile Gly Glu Cys
305                 310                 315                 320

Pro Lys Tyr Val Lys Ser Lys Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Arg Lys Ser
    370                 375                 380

Thr Gln Ser Ala Ile Asp Gly Ile Thr Asn Lys Val Asn Ser Ile Ile
385                 390                 395                 400

Glu Lys Met Asn Ser Gln Phe Thr Ala Val Gly Lys Glu Phe Asn His
                405                 410                 415

Leu Glu Lys Arg Ile Glu Asn Leu Asn Arg Lys Val Asp Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asp Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Glu Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```